(12) United States Patent
Tsutsumi et al.

(10) Patent No.: US 11,617,732 B2
(45) Date of Patent: Apr. 4, 2023

(54) COMPOSITION FOR IMPROVING VASCULAR ENDOTHELIAL FUNCTION

(71) Applicant: NIPPON SUISAN KAISHA, LTD., Tokyo (JP)

(72) Inventors: Rie Tsutsumi, Tokushima (JP); Jiro Takeo, Tokyo (JP); Hiroko Miyahara, Tokyo (JP); Hiroshi Sakaue, Tokushima (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 223 days.

(21) Appl. No.: 16/615,254

(22) PCT Filed: May 23, 2018

(86) PCT No.: PCT/JP2018/019783
§ 371 (c)(1),
(2) Date: Nov. 20, 2019

(87) PCT Pub. No.: WO2018/216715
PCT Pub. Date: Nov. 29, 2018

(65) Prior Publication Data
US 2020/0069625 A1 Mar. 5, 2020

(30) Foreign Application Priority Data
May 23, 2017 (JP) .............................. JP2017-101459

(51) Int. Cl.
*A61K 31/201* (2006.01)
*A61P 9/14* (2006.01)
*A61K 31/231* (2006.01)
*A61K 35/60* (2006.01)

(52) U.S. Cl.
CPC .......... *A61K 31/201* (2013.01); *A61K 31/231* (2013.01); *A61K 35/60* (2013.01); *A61P 9/14* (2018.01)

(58) Field of Classification Search
None
See application file for complete search history.

(56) References Cited

U.S. PATENT DOCUMENTS

2014/0066508 A1  3/2014  Yang et al.

FOREIGN PATENT DOCUMENTS

WO    WO 2012/121080 A1    9/2012

OTHER PUBLICATIONS

Newens (DHA-rich fish oil reverses the detrimental effects of saturated fatty acids on postprandial vascular reactivity, Am J Clin Nutr, 2011; 94:741-8). (Year: 2011).*
Hill (Combining fish-oil supplements with regular aerobic exercise improves body composition and cardiovascular disease risk factors, Am J Clin Nutr 2007;85:1267-74). (Year: 2007).*
International Search Report dated Jul. 3, 2018, in PCT/JP2018/019783.
Bang et al., "The composition of the Eskimo food in north western Greenland," The American Journal of Clinical Nutrition, Dec. 1980, 33(12):2657-2661.
Dyerberg et al., "Fatty acid composition of the plasma lipids in Greenland Eskimos," The American Journal of Clinical Nutrition, Sep. 1975, 28(9):958-966.
Dyerberg et al., "Eicosapentaenoic acid and prevention of thrombosis and atherosclerosis?", The Lancet, Jul. 15, 1978, 2(8081):117-119.
J-ISCP Society, "Vascular endothelial function as a risk prognostic factor," Cardiovascular Drug Therapy, 2015, 3(1):35-43, with English abstract.
Nanri et al., "Fish intake and type 2 diabetes in Japanese men and women: the Japan Public Health Center-based Prospective Study," Am. J. Clin. Nutr., 2011, 94(3):884-891.
Yang et al., "Dietary Saury Oil Reduces Hyperglycemia and Hyperlipidemia in Diabetic KKAγ Mice and in Diet-Induced Obese C57BL/6J Mice by Altering Gene Expression," Lipids, 2011, 46(5):425-434.
Yang et al., "Beneficial Effects of Dietary Fish-Oil-Derived Momounsaturated Fatty Acids on Metabolic Syndrome Risk Factors and Insulin Resistance in Mice," Journal of Agricultural and Food Chemistry, 2011, 59(13):7482-7489.
Yang et al., "Pollock oil supplementation modulates hyperlipidemia and ameliorates hepatic steatosis in mice fed a high-fat diet," Lipids in Health and Disease, 2011, 10:189-198.
Yang et al., "Long-chain monounsaturated fatty acid-rich fish oil attenuates the development of atherosclerosis in mouse models," Mol. Nutr. Food Res., 2016, 60(10):2208-2218.
Yang et al., "Dietary marine-derived long-chain monounsaturated fatty acids and cardiovascular disease risk: a mini review," Lipids in Health and Disease, 2016, 15:201, 1-9.
Yang et al., "Dietary supplementation with long-chain monounsaturated fatty acid isomers decreases atherosclerosis and alters lipoprotein proteomes in LDL$^{-/-}$mice," Atherosclerosis, Apr. 2017, 262:31-38.
Yang et al., "Dietary long-chain monounsaturated fatty acid (LCMUFA) as functional ingredient in fish oils: a novel approach for cardioprotection," The FASEB Journal, Apr. 2017, abstract 1b228.

\* cited by examiner

*Primary Examiner* — Susan Hoffman
*Assistant Examiner* — Jacob A Boeckelman
(74) *Attorney, Agent, or Firm* — Foley & Lardner LLP

(57) ABSTRACT

The present invention provides a composition for improving vascular endothelial function, comprising: an ingredient selected from a monounsaturated fatty acid having 20 carbon atoms or more, a salt thereof, and an ester thereof as an active ingredient, in which the ratio of the monounsaturated fatty acid having 20 carbon atoms or more to the total fatty acids in the composition is 10 wt % or greater. The present invention also provides a composition for improving sleep, comprising an ingredient selected from a monounsaturated fatty acid having 20 carbon atoms or more, a salt thereof, and an ester thereof as an active ingredient.

11 Claims, 5 Drawing Sheets

COMPOSITION FOR IMPROVING VASCULAR ENDOTHELIAL FUNCTION

CROSS-REFERENCE TO RELATED APPLICATIONS

This application is the U.S. National Stage of PCT/JP2018/019783, filed May 23, 2018, which claims priority to JP 2017-101459, filed May 23, 2017.

TECHNICAL FIELD

The present invention relates to a composition for improving vascular endothelial function. The present invention also relates to a composition for improving sleep.

BACKGROUND ART

Fish is known to contain a plenty of an n-3 polyunsaturated fatty acid which is an unsaturated fatty acid. Many studies have been reported to indicate that eating fish frequently reduces a risk of suffering from cardiovascular disease. In particular, the epidemiological study in Greenland is famous as the pioneering epidemiological study in which eicosapentaenoic acid (EPA) which is an n-3 polyunsaturated fatty acid has gained attention in the prevention or treatment of cardiovascular disease. The epidemiological study revealed that there were fewer individuals who developed acute myocardial infarction in the original inhabitants in Greenland, Innuit, and were also less mortality due to ischemic heart disease. Further, as a result of studying their diets, it was revealed that many n-3 polyunsaturated fatty acids, such as EPA and docosahexaenoic acid (DHA), were often consumed by dietary habits of earless seal and fish, and there was less intake of n-6 polyunsaturated fatty acids that were often included in terrestrial animals and plants. It has been reported that the difference in fatty acid composition ingested as a meal was a factor in which the onset rate of acute myocardial infarction and the mortality due to ischemic heart disease in Innuit were low (Non-Patent Documents 1 to 3). In addition, in human clinical trials, the effect of decreasing neutral fat by EPA and DHA have been shown, but it is known that little or no cholesterol-lowering effect is observed.

On the other hand, it has been reported that long chain monounsaturated fatty acids (LC-MUFA) having 20 and 22 carbon atoms, which are known to be rich in saury oil and Alaska pollock oil, have a cholesterol-lowering effect (Patent Document 1). It has also been discovered that dietary induced obesity model mice and type 2 diabetic model mice have been found to have effects such as the reduction of total cholesterol, LDL-cholesterol, neutral fat and blood glucose levels in blood, and the improvement of the insulin resistance by ingesting saury oil and Alaska pollock oil (Non-Patent Document 4 to 6). The similar effect has also been confirmed with oils and fats that LC-MUFA are selectively concentrated (Non-Patent Document 5). In this context, there is a report that increasing the amount of seafood ingestion in men reduces the risk of developing diabetes from cohort study of fifty thousand people of Japanese men and women. In particular, the study also reports that increasing the amount of ingestion of small size and intermediate size fish such as saury and Mackerel and fish having a lot of oils such as salmon reduces the risk (Non-Patent Document 7).

Also, the study with an artery-cure model mice reports that LC-MUFA ingestion suppressed formation of atherosclerotic plaque in the aortic sinus, and that this is likely to be a result of a protective effect combined with the decrease in blood inflammatory cytokine concentration and the promotion of cholesterol removal from macrophages by the stimulation of the PPAR signaling pathway (Non-Patent Document 8). However, no effect on the vascular endothelial function itself due to LC-MUFA ingestion is disclosed in Non-Patent Document 8.

Vascular endothelial cells regulate vasoconstriction and relaxation of vascular walls by secreting vasoactive substances such as nitric oxide (NO) and endothelin. Vascular endothelial cells are also responsible for functions such as maintaining blood pressure and modulating vascular permeability. It is believed that such reduced function of vascular endothelial cells (i.e. vascular endothelial function) leads to a variety of diseases, and is known to be involved in the development and progression of atherosclerosis, for example. In recent years, blood flow-dependent vasodilation reactions (Flow Mediated Dilation (FMD)) test has been focused on non-invasive vascular endothelial function studies. A subject with a low FMD value is considered to be susceptible to events of the cardiovascular vessel (Non-Patent Document 9). The FMD tests has also been insurance-applied in Japan and have been used for early discovery and early treatment of various diseases based on atherosclerosis.

CITATION LIST

Patent Documents

Patent Document 1: Re-publication of PCT International Publication No. 2012-121080

Non-Patent Documents

Non-Patent Document 1: Dyerberg J, Bang H O, Hjorne N: Fatty acid composition of the plasma lipids in Greenland Eskimos. Am J Clin Nutr., 28 (9): 958-66, 1975.

Non-Patent Document 2: Dyerberg J, Bang H O, Stoffersen E, Moncada S, Vane J R: Eicosapentaenoic acid and prevention of thrombosis and atherosclerosis. Lancet, 2 (8081): 117-9, 1978.

Non-Patent Document 3: Bang H O, Dyerberg J, Sinclair H M: The composition of the Eskimo food in north western Greenland. Am J Clin Nutr., 33 (12): 2657-61, 1980.

Non-Patent Document 4: Yang Z H, Miyahara H, Takemura S, Hatanaka A: Dietary saury oil reduces hyperglycemia and hyperlipidemia in diabetic KKAy mice and in diet-induced obese C57BL/6J mice by altering gene expression. Lipids, 46 (5): 425-34, 2011.

Non-Patent Document 5: Yang Z H, Miyahara H, Mori T, Doisaki N, Hatanaka A: Beneficial effects of dietary fish-oil-derived monounsaturated fatty acids on metabolic syndrome risk factors and insulin resistance in mice. J Agric Food Chem., 59 (13): 7482-9, 2011.

Non-Patent Document 6: Yang Z H, Miyahara H, Takeo J, Hatanaka A, Katayama M: Pollock oil supplementation modulates hyperlipidemia and ameliorates hepatic steatosis in mice fed a high-fat diet. Lipids Health Dis., 10: 189-98, 2011.

Non-Patent Document 7: Nanri A, Mizoue T, Noda M, Takahashi Y, Matsushita Y, Poudel-Tandukar K, Kato M, Oba S, Inoue M, Tsugane S: Fish intake and type 2 diabetes in Japanese men and women: the Japan Public Health Center-based Prospective Study. Am J Clin Nutr., 94 (3): 884-91, 2011.

Non-Patent Document 8: Yang Z H, Bando M, Sakurai T, Chen Y, Emma-Okon B, Wilhite B, Fukuda D, Vaisman B, Pryor M, Wakabayashi Y, Sampson M, Zu-Xi Yu, Sakurai A, Zarzour A, Miyahara H, Takeo J, Sakaue H, Sata M, Remaley A T: Long-chain monounsaturated fatty acid-rich fish oil attenuates the development of atherosclerosis in mouse models. Mol Nutr Food Res., 0: 1-11, 2016.

Non-Patent Document 9: J-ISCP Society, "cardiovascular drug therapy", 3 (1), 35-43 (2015).

SUMMARY OF INVENTION

Technical Problem

Disease due to reduced vascular endothelial function has recently become a problem, and there has been a demand for an approach to improve the vascular endothelial function that is safe and can be performed over a long period of time.

In addition, among LC-MUFA, positional isomers such as C20:1n-11 and C22:1n-11 are also included in fish oils from fish species such as Alaska pollock, Mackerel, and salmon in addition to saury, but they are not almost included in plant oils. Because saury and Alaska pollock are highly popular fish in Japanese and fish with high industrial value, there is a strong desire to develop new applications for fish oils that are enriched in LC-MUFA, which are prepared from these fish species.

An object of the present invention is to provide novel applications of components of fish oils, including LC-MUFA, in particular for health-promoting applications.

Solution to Problem

As a result of diligent research to achieve the above object, the inventors have found that a Flow Mediated Dilation was improved by ingesting saury oil that is enriched in LC-MUFA. While reports have previously been made on the effect of EPA and DHA on vascular endothelial function, LC-MUFA rich oils has not been known to affect vascular endothelial function.

The inventors have also found that morning awake was improved by ingesting saury oil that LC-MUFA was rich. To date, LC-MUFA rich oils has not been known to affect sleep.

The inventors have further studied based on these findings, and completed the present invention.

Therefore, the present invention is as follows.

[1] A composition for improving vascular endothelial function, including
an ingredient selected from a monounsaturated fatty acid having 20 carbon atoms or more, a salt thereof, and an ester thereof as an active ingredient, in which
the ratio of the monounsaturated fatty acid having 20 carbon atoms or more to the total fatty acids in the composition is 10 wt % or greater.

[2] The composition according to [1], in which the active ingredient is an ingredient selected from a monounsaturated fatty acid having 20 carbon atoms, a salt thereof, and an ester thereof, an ingredient selected from a monounsaturated fatty acid having 22 carbon atoms, a salt thereof, and an ester thereof, or combinations thereof.

[3] The composition according to [1] or [2], in which the active ingredient is a glyceride containing the monounsaturated fatty acid having 20 carbon atoms or more as a constituent fatty acid.

[4] The composition according to [3], in which the glyceride is a triglyceride.

[5] The composition according to any one of [1] to [4], further including an n-3 polyunsaturated fatty acid and an n-6 polyunsaturated fatty acid, in which the area ratio of the n-3 polyunsaturated fatty acid to the n-6 polyunsaturated fatty acid is 4.0 or greater.

[6] The composition according to any one of [1] to [5], in which the active ingredient is derived from a fish oil.

[7] The composition according to [6], in which the fish oil is a saury oil.

[8] The composition according to any one of [1] to [7], in which the active ingredient is orally administered for four weeks or more in an amount of 2 mg/kg weight/day or greater, based on the monounsaturated fatty acid having 20 carbon atoms or more.

[9] The composition according to any one of [1] to [8], in which the composition is for improving Flow Mediated Dilation.

[10] The composition according to any one of [1] to [9], in which the composition is for reducing a possibility of suffering from a disease due to vascular endothelial disorders.

[11] The composition according to any one of [1] to [10], in which the composition is a food composition.

[12] The composition according to any one of [1] to [10], in which the composition is a pharmaceutical composition.

[13] A composition for improving sleep, comprising an ingredient selected from a monounsaturated fatty acid having 20 carbon atoms or more, a salt thereof, and an ester thereof as an active ingredient.

[14] The composition according to [13], in which the active ingredient is an ingredient selected from a monounsaturated fatty acid having 20 carbon atoms, a salt thereof, and an ester thereof, an ingredient selected from a monounsaturated fatty acid having 22 carbon atoms, a salt thereof, and an ester thereof, or combinations thereof.

[15] The composition according to [13] or [14], in which the active ingredient is a glyceride containing the monounsaturated fatty acid having 20 carbon atoms or more as a constituent fatty acid.

[16] The composition according to [15], in which the glyceride is a triglyceride.

[17] The composition according to any one of [13] to [16], in which the ratio of the monounsaturated fatty acid having 20 carbon atoms or more to the total fatty acids in the composition is 10 wt % or greater.

[18] The composition according to any one of [13] to [17], further including an n-3 polyunsaturated fatty acid and an n-6 polyunsaturated fatty acid, in which the area ratio of the n-3 polyunsaturated fatty acid to the n-6 polyunsaturated fatty acid is 4.0 or greater.

[19] The composition according to any one of [13] to [18], in which the active ingredient is derived from a fish oil.

[20] The composition according to [19], in which the fish oil is a saury oil.

[21] The composition according to any one of [13] to [20], in which the composition is used such that the active ingredient is orally administered for four weeks or more in an amount of 2 mg/kg weight/day or greater, based on the monounsaturated fatty acid having 20 carbon atoms or more.

[22] The composition according to any one of [13] to [21], in which the composition is for improving awake.

[23] The composition according to any one of [13] to [22], in which the composition is a food composition.

[24] The composition according to any one of [13] to [22], in which the composition is a pharmaceutical composition.

[25] A method of improving vascular endothelial function, including:

administering a composition comprising an effective amount of an ingredient selected from a monounsaturated fatty acid having 20 carbon atoms or more, a salt thereof, and an ester thereof as an active ingredient to a subject, in which the ratio of the monounsaturated fatty acid having 20 carbon atoms or more to the total fatty acids in the composition is 10 wt % or greater.

[26] The method according to [25], in which the active ingredient is an ingredient selected from a monounsaturated fatty acid having 20 carbon atoms, a salt thereof, and an ester thereof, an ingredient selected from a monounsaturated fatty acid having 22 carbon atoms, a salt thereof, and an ester thereof, or combinations thereof.

[27] The method according to [25] or [26], in which the active ingredient is a glyceride containing the monounsaturated fatty acid having 20 carbon atoms or more as a constituent fatty acid.

[28] The method according to [27], in which the glyceride is a triglyceride.

[29] The method according to any one of [25] to [28], in which the composition further includes an n-3 polyunsaturated fatty acid and an n-6 polyunsaturated fatty acid, and wherein the area ratio of the n-3 polyunsaturated fatty acid to the n-6 polyunsaturated fatty acid is 4.0 or greater.

[30] The method according to any one of [25] to [29], in which the active ingredient is derived from a fish oil.

[31] The method according to [30], in which the fish oil is a saury oil.

[32] The method according to any one of [25] to [31], including orally administering the active ingredient for four weeks or more in an amount of 2 mg/kg weight/day or greater, based on the monounsaturated fatty acid having 20 carbon atoms or more.

[33] The method according to any one of [25] to [32], in which the composition is for improving Flow Mediated Dilation.

[34] The method according to any one of [25] to [33], in which the composition is for reducing a possibility of suffering from a disease due to vascular endothelial disorders.

[35] The method according to any one of [25] to [34], in which the composition is a food composition.

[36] The method according to any one of [25] to [34], in which the composition is a pharmaceutical composition.

[37] Use of an ingredient selected from a monounsaturated fatty acid having 20 carbon atoms or more, a salt thereof, or an ester thereof for producing a composition for improving vascular endothelial function, in which the ratio of the monounsaturated fatty acid having 20 carbon atoms or more to the total fatty acids in the composition is 10 wt % or greater.

[38] The use according to [38], in which the monounsaturated fatty acid having 20 carbon atoms or more, a salt thereof, or an ester thereof is an ingredient selected from a monounsaturated fatty acid having 20 carbon atoms, a salt thereof, and an ester thereof, an ingredient selected from a monounsaturated fatty acid having 22 carbon atoms, a salt thereof, and an ester thereof, or combinations thereof.

[39] The use according to [37] or [38], in which the monounsaturated fatty acid having 20 carbon atoms or more, a salt thereof, and an ester thereof is a glyceride containing the monounsaturated fatty acid having 20 carbon atoms or more as a constituent fatty acid.

[40] The use according to [39], in which the glyceride is a triglyceride.

[41] The use according to any one of [37] to [40], in which the composition further includes an n-3 polyunsaturated fatty acid and an n-6 polyunsaturated fatty acid, and wherein the area ratio of the n-3 polyunsaturated fatty acid to the n-6 polyunsaturated fatty acid is 4.0 or greater.

[42] The use according to any one of [37] to [41], in which the monounsaturated fatty acid having 20 carbon atoms or more, a salt thereof, or an ester thereof is derived from a fish oil.

[43] The use according to [42], in which the fish oil is a saury oil.

[44] The use according to any one of [37] to [43], in which the composition is used such that the monounsaturated fatty acid having 20 carbon atoms or more, a salt thereof, or an ester thereof is orally administered for four weeks or more in an amount of 2 mg/kg weight/day or greater, based on the monounsaturated fatty acid having 20 carbon atoms or more.

[45] The use according to any one of [37] to [44], in which the composition is for improving Flow Mediated Dilation.

[46] The use according to any one of [37] to [45], in which the composition is for reducing a possibility of suffering from a disease due to vascular endothelial disorders.

[47] The use according to any one of [37] to [46], in which the composition is a food composition.

[48] The use according to any one of [37] to [46], in which the composition is a pharmaceutical composition.

[49] A method for improving sleep, including administering a composition comprising an effective amount of an ingredient selected from a monounsaturated fatty acid having 20 carbon atoms or more, a salt thereof, and an ester thereof as an active ingredient to a subject.

[50] The method according to [49], in which the active ingredient is an ingredient selected from a monounsaturated fatty acid having 20 carbon atoms, a salt thereof, and an ester thereof, an ingredient selected from a monounsaturated fatty acid having 22 carbon atoms, a salt thereof, and an ester thereof, or combinations thereof.

[51] The method according to [49] or [50], in which the active ingredient is a glyceride containing the monounsaturated fatty acid having 20 carbon atoms or more as a constituent fatty acid.

[52] The method according to [51], in which the glyceride is a triglyceride.

[53] The method according to any one of [49] to [52], in which the ratio of the monounsaturated fatty acid having 20 carbon atoms or more to the total fatty acids in the composition is 10 wt % or greater.

[54] The method according to any one of [49] to [53], in which the composition further includes an n-3 polyunsaturated fatty acid and an n-6 polyunsaturated fatty acid, and wherein the area ratio of the n-3 polyunsaturated fatty acid to the n-6 polyunsaturated fatty acid is 4.0 or greater.

[55] The method according to any one of [49] to [54], in which the active ingredient is derived from a fish oil.

[56] The method according to [55], in which the fish oil is a saury oil.

[57] The method according to any one of [49] to [56], including orally administering the active ingredient for four weeks or more in an amount of 2 mg/kg weight/day or more, based on the monounsaturated fatty acid having 20 carbon atoms or more.

[58] The method according to any one of [49] to [57], in which the composition is for improving awake.

[59] The method according to any one of [49] to [58], in which the composition is a food composition.

[60] The method according to any one of [49] to [58], in which the composition is a pharmaceutical composition.

[61] Use of a monounsaturated fatty acid having 20 carbon atoms or more, a salt thereof, or an ester thereof for producing a composition for improving sleep.

[62] The use according to [61], in which the monounsaturated fatty acid having 20 carbon atoms or more, a salt thereof, or an ester thereof is an ingredient selected from a monounsaturated fatty acid having 20 carbon atoms, a salt thereof, and an ester thereof, an ingredient selected from a monounsaturated fatty acid having 22 carbon atoms, a salt thereof, and an ester thereof, or combinations thereof.

[63] The use according to [61] or [62], in which the monounsaturated fatty acid having 20 carbon atoms or more, a salt thereof, or an ester thereof is a glyceride containing the monounsaturated fatty acid having 20 carbon atoms or more as a constituent fatty acid.

[64] The use according to [63], in which the glyceride is a triglyceride.

[65] The use according to any one of [61] to [64], in which the ratio of the monounsaturated fatty acid having 20 carbon atoms or more to the total fatty acids in the composition is 10 wt % or greater.

[66] The use according to any one of [61] to [65], in which the composition further includes an n-3 polyunsaturated fatty acid and an n-6 polyunsaturated fatty acid, and wherein the area ratio of the n-3 polyunsaturated fatty acid to the n-6 polyunsaturated fatty acid is 4.0 or greater.

[67] The use according to any one of [61] to [66], in which the monounsaturated fatty acid having 20 carbon atoms or more, a salt thereof, or an ester thereof is derived from a fish oil.

[68] The use according to [67], in which the fish oil is a saury oil.

[69] The use according to any one of [61] to [68], in which the composition is used so that the monounsaturated fatty acid having 20 carbon atoms or more, a salt thereof, or an ester thereof is orally administered for four weeks or more in an amount of 2 mg/kg weight/day or greater, based on the monounsaturated fatty acid having 20 carbon atoms or more.

[70] The method according to any one of [61] to [69], in which the composition is for improving awake.

[71] The use according to any one of [61] to [70], in which the composition is a food composition.

[72] The use according to any one of [61] to [70], in which the composition is a pharmaceutical composition.

Advantageous Effects of Invention

In accordance with the present invention, there is provided a composition for improving vascular endothelial function containing components of LC-MUFA rich fish oil, such as saury oil. The composition can reduce the possibility of suffering from a disease due to vascular endothelial disorders.

Also in accordance with the present invention, there is provided a composition for improving sleep containing components of LC-MUFA rich fish oil, such as saury oil. The composition can provide good sleep and in particular healthcare health enhancement.

BRIEF DESCRIPTION OF DRAWINGS

FIG. 1-2 is a diagram representing changes in FMD values of subjects before and after ingestion, when the subjects ingested the can of the saury of Example 1. The figure shows the FMD values increased by about 12% after ingestion.

FIG. 1-3 is a diagram representing changes in FMD values of six subjects before and after ingestion and after a 1 month wash-out period after the end of consumption, in which six subjects have increased FMD values after ingestion among subjects ingesting the capsule of the saury oil of Example 1. The figure illustrates that the FMD values increased by about 82% after ingestion, and that the value decreased by 20% after the washout period. The single black star indicates the significant difference (p=0.0402).

FIG. 1-4 is a diagram representing changes in FMD values of three subjects before and after ingestion and after a 1 month wash-out period after the end of consumption, in which three subjects have increased FMD values after ingestion among subjects ingesting the can of the saury of Example 1. The figure illustrates that the FMD values increased by about 66% after ingestion, and the value decreased by 18% after the washout period.

FIG. 1-5 is a diagram representing changes in FMD values of four subjects before and after ingestion, in which the four subjects have FMD values outside of normal range (less than 6%) before ingestion and suspected vascular endothelial disorder among subjects ingesting the capsule of the saury oil of Example 1. The figure illustrates the FMD values increased by about 253% after ingestion.

FIG. 1-6 is a diagram representing changes in FMD values of four subjects before and after ingestion, in which the four subjects have FMD values outside of normal range (less than 6%) before ingestion and suspected vascular endothelial disorder among subjects ingesting the can of the saury of Example 1. The figure illustrates the FMD values increased by about 45% after ingestion.

FIG. 2 is a diagram representing changes in wakefulness of subjects before and after ingestion, when the subjects ingested the capsule of the saury oil of Example 1. It is a relative quantified evaluation of the mood upon wake-up of the subject when the condition in which the subject can wake up comfortably in the morning is taken as 100, and the condition in which the subject can not wake up comfortably at all is taken as 0. Higher values indicate better awake. The figure illustrates morning awake was 14% improved after ingestion compared to before ingestion.

FIG. 3 is a diagram representing changes in somatic fat volumes of subjects before and after ingestion, when the subjects ingested the capsule of the saury oil of Example 1. The figure illustrates the somatic fat volumes decreased by about 0.7% after ingestion. The double black stars indicate the significant difference (p=0.0057).

FIG. 4 is a diagram representing changes in FMD values of subjects before and after ingestion, when the subjects ingested the capsule of the saury oil or the capsule of blended oil of Example 2. *** indicates the significant difference (p=0.0008).

DESCRIPTION OF EMBODIMENTS

Figure 1:
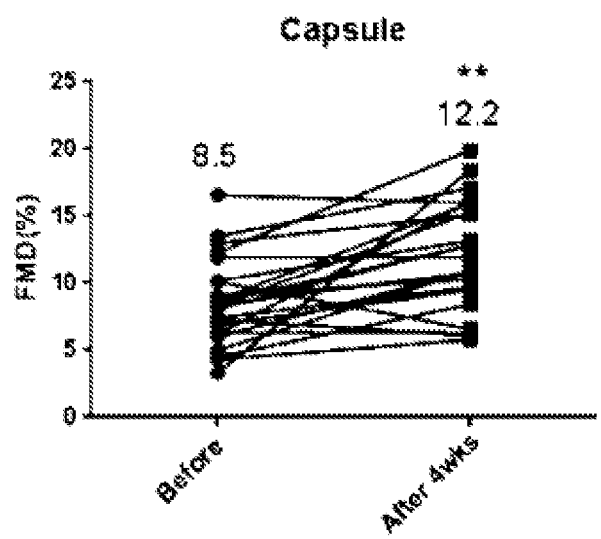
FIG. 1-1 is a diagram representing changes in FMD values of subjects before and after ingestion, when the subjects ingested the capsule of the saury oil of Example 1. The figure illustrates the FMD values increased by about 44% after ingestion. The double black starts indicate the significant difference (p=0.0003).

The present invention will be specifically described below.

Note that the following abbreviations may be used herein:
MUFA: Monounsaturated fatty acid
LC-MUFA: Long chain monounsaturated fatty acid, in particular, the generic name of isomers of C20:1 and C22:1
PUFA: polyunsaturated fatty acid Composition for Improving Vascular Endothelial Function The present invention provides a composition for improving vascular endothelial function, including an ingredient selected from a monounsaturated fatty acid having 20 carbon atoms or more, a salt thereof, and an ester thereof as an active ingredient, in which the ratio of the monounsaturated fatty acid having 20 carbon atoms or more to the total fatty acids in the composition is 10 wt % or greater (hereinafter may be referred to as "composition for improving vascular endothelial function according to an embodiment of the present invention").

The monounsaturated fatty acid having 20 carbon atoms or more, a salt thereof, or an ester thereof used in an embodiment of the present invention is not particularly limited as long as they may be acceptable for pharmaceutical use or food use. The glyceride containing the monounsaturated fatty acid having 20 carbon atoms or more as the constituent fatty acid can be produced by known methods. For example, the glyceride can be also produced as oil and fats derived from natural products by the boiling and extracting method described in WO 1996/26647. Oil and fats derived from natural products include marine oils (e.g., fish oils such as saury oil, fats and oils of mammals such as earless seal and whale), and microbial oils. As described below, fish oils have a high content of monounsaturated fatty acids having 20 carbon atoms or more. Therefore, it is preferred that the active ingredient in the composition for improving vascular endothelial function according to an embodiment of the present invention is derived from fish oils (e.g. saury oil). In addition, free monounsaturated fatty acids having 20 carbon atoms or more, a salt thereof, and esters other than glycerides can be prepared by known methods using, for example, the glyceride described above as the raw material.

For example, saury crude oil is typically taken by the following method, similar to other fish oils. Whole saury or the processed residues such as fish heads, skins, backbones, and viscus gained by fish processing are crushed, steamed and simmered, and then squeezed to separate them into broth (stickwater, SW) and squeezed meal. The oil and fat obtained together with the broth are separated from the broth by centrifugal separation.

The Standard Tables of Food Composition in Japan, 2015 Version (Seven Revised Edition) describes that fatty acids of saury (with skins, raw) contain 26.0 wt % of docosenoic acid (C22:1), 17.6 wt % of icosenoic acid (C20:1), and the total amount of monounsaturated fatty acids is 54.2 wt %. Saury oil is characterized by having a larger content of monounsaturated fatty acids among fish oils.

The crude oil of fish oil is converted to a refined fish oil by purification steps such as degum, deacid, bleaching, and deodorizing. The refined fish oil can also be used as a source for the ingredient selected from a monounsaturated fatty acid having 20 carbon atoms or more, a salt thereof, and an ester thereof.

In one aspect, an oil having higher concentration of the monounsaturated fatty acid may be used as a source for the ingredient selected from a monounsaturated fatty acid having 20 carbon atoms or more, a salt thereof, and an ester thereof. In this case, an MUFA concentrated triglyceride can be obtained by a method of concentrating using a lipase reaction, or a method of ethyl-esterificating of the monounsaturated fatty acid and concentrating the ethyl ester, and then trans-esterifying with glycerin to reconstitute into the triglyceride.

Monounsaturated fatty acids having 20 carbon atoms or more include monounsaturated fatty acids having 20 carbon atoms (C20:1) (for example, C20:1 n-11, C20:1 n-9, and C20:1 n-7), monounsaturated fatty acids having 22 carbon atoms (C22:1) (for example, C22:1 n-11, C22:1 n-9, C22:1 n-7, and C22:1 n-13), and monounsaturated fatty acids having 24 carbon atoms (C24:1) (for example, C24:1 n-9). In a preferred aspect, the active ingredient of the composition for improving vascular endothelial function according to an embodiment of the present invention is an ingredient selected from C20:1, a salt thereof, and an ester thereof, an ingredient selected from C22:1, a salt thereof, and an ester thereof, or combination thereof.

The content of C22:1 and C20:1 varies depending on the type of fish. Examples of fish with the high content of C22:1 and C20:1 include fish of Scomberesocidae such as saury, fish of Gadidae such as Pacific cod, Alaska pollock, Atlantic cod, and Sablefish, fish of Salmonida such as Chum salmon, Silver salmon, Sockeye salmon, pink salmon, Atlantic Salmon, and Rainbow trout, fish of Osmeriformes such as Capellin and Smelt, and Clupeidae such as Pacific herring. In addition, a relatively large amount of LC-MUFAs is also contained in fish such as Sand lance, tuna, Mackerel, and Alfonsino. A large amount of LC-MUFAs is also contained in liver oil of sharks such as spiny dogfish, basking shark, and silver chimaera. In an embodiment of the present invention, fish oils prepared from these fish can be used as they are, or can be used after purifying or concentrating.

The ratio of the monounsaturated fatty acid having 20 carbon atoms or more to the total fatty acids in the composition for improving vascular endothelial function according to an embodiment of the present invention is 10 wt % or greater, for example, 11 wt % or greater, 12 wt % or greater, 13 wt % or greater, 14 wt % or greater, 15 wt % or greater, 16 wt % or greater, 17 wt % or greater, 18 wt % or greater, 19 wt % or greater, 20 wt % or greater, 21 wt % or greater, 22 wt % or greater, 23 wt % or greater, 24 wt % or greater, 25 wt % or greater, 26 wt % or greater, 27 wt % or greater, 28 wt % or greater, 29 wt % or greater, 30 wt % or greater, 40 wt % or greater, 50 wt % or greater, 60 wt % or greater, 70 wt % or greater, 80 wt % or greater, or 90 wt % or greater.

In an embodiment of the present specification, the ratio of the fatty acid to the total fatty acids in the composition (wt %) is calculated by the value measured by gas chromatography after esterifying the ingredient in the composition according to AOCS official method Ce1b-89, unless otherwise specified. By the content of fatty acids, it also means the ratio of the fatty acid (wt %) to the total fatty acids described above. The analytical conditions used for gas chromatography are listed below.

Instrument: Agilent 6890 GC system (Agilent Technologies)
Column: DB-WAX (Agilent Technologies, 30 m×0.25 mm ID, 0.25 μm film thickness)
Carrier gas: helium (1.0 mL/min, constant flow)
Inlet temperature: 250° C.
Injected quantity of sample: 1 μL
Injection method: split
Split ratio: 20:1

Column oven: 180° C.—3° C./min—230° C.
Detector: FID
Detector temperature: 250° C.

Examples of salts of the monounsaturated fatty acid having 20 carbon atoms or more in an embodiment of the present invention include potassium salts and sodium salts. In addition, examples of esters of the monounsaturated fatty acid having 20 carbon atoms or more include esters of a lower alcohol having 5 carbon atoms or less (for example, methyl esters, ethyl esters, n-propyl esters, i-propyl esters, n-butyl esters, s-butyl esters, t-butyl esters, and n-pentyl esters), esters with glycerin such as monoglycerides, diglycerides, and triglycerides (i.e., glycerides), and phospholipids. In a preferred aspect, the active ingredient of the composition for improving vascular endothelial function according to an embodiment of the present invention is a glyceride containing a monounsaturated fatty acid having from 20 carbon atoms or more as the constituent fatty acid, and more preferably triglycerides.

As the monounsaturated fatty acid having from 20 carbon atoms or more in the present invention, oils and fats derived from natural products containing free monounsaturated fatty acids having from 20 carbon atoms or more can be used as they are, or can be used after purifying or concentrating. In addition, as esters of the monounsaturated fatty acid having 20 carbon atoms or more, oil and fats derived from natural products containing a glyceride containing monounsaturated fatty acids having from 20 carbon atoms or more as the constituent fatty acid can be used as they are, or can be used after purifying or concentrating.

Furthermore, a fractionated oil obtained by esterifying oil and fats derived from natural products and then fractionating them by high performance liquid chromatography can be used as esters of the monounsaturated fatty acid having 20 carbon atoms or more. Fractionated oils include C20:1 concentrated fractionated oils, C22:1 concentrated fractionated oils, and C24:1 concentrated fractionated oils.

The composition for improving vascular endothelial function according to an embodiment of the present invention may further include an n-3 polyunsaturated fatty acid and an n-6 polyunsaturated fatty acid. In this case, the area ratio of the n-3 polyunsaturated fatty acid to the n-6 polyunsaturated fatty acid is 4.0 or greater, for example, 5.0 or greater, 6.0 or greater, 7.0 or greater, 8.0 or greater, 9.0 or greater, or 10.0 or greater. In the present specification, the n-3 polyunsaturated fatty acid is a polyunsaturated fatty acid having 18 carbon atoms or more and having two or more carbon-carbon double bonds, and having the first double bond between the third and the fourth carbon atoms, numbering from the carbon of methyl group in the terminal of fatty acid chain. Examples include α-linolenic acid (C18:3 n-3), octadecatetraenoic acid (C18:4 n-3), eicosatetraenoic acid (C20:4 n-3), eicosapentaenoic acid (C20:5 n-3), docosapentaenoic acid (C22:5 n-3), and docosahexaenoic acid (C22:6 n-3). In addition, the n-6 polyunsaturated fatty acid is a polyunsaturated fatty acid having 18 carbon atoms or more and having two or more carbon-carbon double bonds, and having the first double bond between the sixth and the seventh carbon atoms, numbering from the carbon of methyl group in the terminal of fatty acid chain. Examples include linoleic acid (C18:2 n-6), and arachidonic acid (C20:4 n-6). In the present specification, the area ratio of the fatty acid refers to the ratio of the peak area detected by gas chromatography after esterifying the fatty acid in the composition according to AOCS official method Ce1b-89. The analytical conditions used for gas chromatography are listed above.

In an embodiment of the present invention, improving vascular endothelial function refers to improving the function of vascular endothelial cells, for example, improving the function of regulating vasoconstriction and relaxation of vascular walls by secreting vasoactive substances such as nitric oxide (NO) and endothelin. As methods for assessing the function of such vascular endothelial cells (vascular endothelial function), for example, strain-gauged plethysmography, FMD (flow-mediated dilatation), and RH-PAT (reactive hyperemia peripheral arterial tonometry) are known ("Guideline for the Noninvasive Assessment of Vascular Function", guideline 2013 for diagnosis and treatment of cardiovascular disease, p. 3 to 112, The Japanese Circulation Society). In a preferred aspect of the invention, FMD is used for assessing vascular endothelial function. The FMD value (%) is the ratio of the maximum expanded width to the resting vessel diameter and is calculated by the following equation:

$$\text{FMD Value (\%)} = \text{maximum expanded width (mm)} / \text{resting vessel diameter (mm)} \times 100$$

The composition for improving vascular endothelial function according to an embodiment of the present invention can be used as a composition for improving Flow Mediated Dilation, because the composition can improve the FMD value.

The test in the Examples described below is directed to healthy individuals. Improving FMD value in the test is not meant to treat diseases such as arteriosclerosis, but may further encourage normal vascular endothelial function or improve the condition of vascular endothelial disorders, and thereby reduce the risk of suffering from a disease due to vascular endothelial disorders. Thus, in one aspect, the composition for improving vascular endothelial function according to an embodiment of the present invention is a composition for reducing the possibility of suffering from a disease due to vascular endothelial disorders. Here, vascular endothelial disorders refer to a condition in which arterial sclerosis has not been achieved, but the vascular endothelial function is reduced. For example, even if no atherosclerotic plaque is found in the blood vessel, it is suspected to be vascular endothelial disorder when the FMD value is less than 5%. The disease due to vascular endothelial disorders includes cardiovascular diseases such as arterial sclerosis, hypertension, periodontal disease, type 2 diabetes, and hyperlipidemia.

The subject for administering the composition for improving vascular endothelial function according to an embodiment of the present invention is a mammal, and preferably a human. The age of the subject to be administered is not particularly limited as long as the effect of the present invention can be achieved. In one aspect, the age of the subject to be administered is 20 or greater, for example, 25 or greater, 30 or greater, 35 or greater, 40 or greater, 45 or greater, 50 or greater, 55 or greater, and 60 or greater.

When the monounsaturated fatty acid having 20 carbon atoms or more, a salt thereof, or an ester thereof is administered to a subject having a FMD value of less than 6%, the effect of improving the FMD value may be more significant. Thus, in one aspect, the subject for administering the composition for improving vascular endothelial function according to an embodiment of the present invention has an FMD value of less than 6%. For example, the age of the subject to be administered may be 20 or greater, for example, 25 or greater, 30 or greater, 35 or greater, 40 or greater, 45 or greater, 50 or greater, 55 or greater, and 60 or greater and the subject may have an FMD value of less than 6%.

The composition for improving vascular endothelial function according to an embodiment of the present invention can be prepared in the form suitable for a pharmaceutical composition, a food composition (for example, functional food products, health food products, and supplements), various solid formulations such as a granule (including a dry syrup), a capsule (soft capsule or hard capsule), a tablet (including a chewable tablet), a powder (a powder formulation), and a pill, or liquid formulations such as oral liquid formulations (including a liquid, a suspension, and a syrup). For example, the composition for improving vascular endothelial function according to an embodiment of the present invention can be formulated as a soft capsule in which a purified fish oil is filled into a gelatin coating.

Examples of additives that help with formulation include excipients, lubricants, binders, disintegrating agents, fluidization agents, dispersing agents, wetting agents, preservatives, thickening agents, pH adjusting agents, colorants, corrigents, surfactants, and solubilization agents. Additionally, prepared as a liquid formulation, thickening agents such as pectin, xanthan gum, guar gum, and the like can be compounded. Moreover, the composition for improving vascular endothelial function according to an embodiment of the present invention can be formed into a coated tablet formulation by using a coating agent, or be formed into a paste-like gelatin formulation. Furthermore, even when preparing the composition for improving vascular endothelial function according to an embodiment of the present invention in other forms, it is sufficient to follow known methods.

The composition for improving vascular endothelial function according to an embodiment of the present invention can take the form of a food composition. In an embodiment of the present invention, the food composition means general food products including beverages. The food composition includes foods for specified health uses and foods with nutrient function defined in the health-promoting food regulations of the Consumer Affairs Agency in addition to general food products including health food products such as supplements. For example, functional food products are provided that have an indication that they have an improved effect on vascular endothelial function. For example, fish oil-containing food products can be provided as are. The food composition according to an embodiment of the present invention also includes a food material for imparting an improved effect in vascular endothelial function by adding, mixing or applying to other food products. In addition to food products, it can also be provided as animal feeds or the like.

When the composition for improving vascular endothelial function according to an embodiment of the present invention is in the form of a food product, the food product is not particularly limited. The food product may be beverages, confectionaries, breads, or soups. Examples include common retort foods, frozen food, ready-to-drink (such as noodles), cans, sausage, cookies, biscuits, cereal bars, crackers, snacks (such as potato chips), pastry, cakes, pies, candies, chewing gum (including pellets and sticks), jellies, soups, ices, dressings, yogurts, or the like, supplements in the form of a tablet, a capsule, and an emulsion, and soft drinks. The method for manufacturing these food products is not particularly limited as long as the effect of the present invention is not impaired, and may be according to the method used by the person skilled in the art for each food products.

It is within the scope of the invention to display the benefits according to an embodiment of the composition for improving vascular endothelial function according to an embodiment of the present invention in packaging containers, product instructions, and brochures and to sell the products according to the present invention. It is also within the scope of the present invention to display the benefits of the present invention on television, Internet websites, brochures, newspaper, magazines, and to advertise and sell the products according to an embodiment of the present invention.

The amount of the ingredient selected from a monounsaturated fatty acid having 20 carbon atoms or more, a salt thereof, and an ester thereof ingested by the subject in an embodiment of the present invention is not particularly limited. For example, the ingredient is ingested in an amount equal to or greater than the effective amount for obtaining the desired effect. Here, the effective amount for obtaining the desired effect refers to the amount required to improve vascular endothelial function. For example, in the case of an adult, depending on the conditions such as age, weight, and health conditions of the subject, 2 mg/kg weight/day or greater, for example, 3 mg/kg weight/day or greater, 4 mg/kg weight/day or greater, 5 mg/kg weight/day or greater, 6 mg/kg weight/day or greater, 7 mg/kg weight/day or greater, 8 mg/kg weight/day or greater, 9 mg/kg weight/day or greater, 10 mg/kg weight/day or greater, 11 mg/kg weight/day or greater, 12 mg/kg weight/day or greater, 13 mg/kg weight/day or greater, 14 mg/kg weight/day or greater, 15 mg/kg weight/day or greater, 16 mg/kg weight/day or greater, 17 mg/kg weight/day or greater, 18 mg/kg weight/day or greater, 19 mg/kg weight/day or greater, 20 mg/kg weight/day or greater, 21 mg/kg weight/day or greater, 22 mg/kg weight/day or greater, 23 mg/kg weight/day or greater, 24 mg/kg weight/day or greater, 25 mg/kg weight/day or greater, 30 mg/kg weight/day or greater, 40 mg/kg weight/day or greater, 50 mg/kg weight/day or greater, 100 mg/kg weight/day or greater, or 200 mg/kg weight/day or greater of the active ingredient based on the monounsaturated fatty acid having 20 carbon atoms or more can be ingested for 4 weeks or more, for example, 5 weeks or more, 6 weeks or more, 7 weeks or more, 8 weeks or more, 9 weeks or more, 10 weeks or more, 11 weeks or more, 12 weeks or more. In addition, since the ingredient selected from a monounsaturated fatty acid having 20 carbon atoms or more, a salt thereof, and an ester thereof does not have a strong side effect, there is no restriction on the daily amount of ingestion.

Composition for Improving Sleep

The present invention also provides a composition for improving sleep, comprising an ingredient selected from a monounsaturated fatty acid having 20 carbon atoms or more, a salt thereof, and an ester thereof as an active ingredient (hereinafter may be referred to as "composition for improving sleep according to an embodiment of the present invention").

The monounsaturated fatty acid having 20 carbon atoms or more, a salt thereof, or an ester thereof used in an embodiment of the present invention is not particularly limited as long as they may be acceptable for pharmaceutical use or food use. The glyceride containing the monounsaturated fatty acid having 20 carbon atoms or more as the constituent fatty acid can be produced by known methods. For example, the glyceride can be also produced as oils and fats derived from natural products by the boiling and extracting method described in WO 1996/26647. Oils and fats derived from natural products include marine oils (e.g., fish oils such as saury oil, oils and fats of mammals such as earless seal and whale), and microbial oils. As described below, fish oils have a high content of monounsaturated fatty acids having 20 carbon atoms or more. Therefore, it is preferred that the active ingredient in the composition for improving sleep of the present invention is derived from fish oils (e.g. saury oil). In addition, free monounsaturated fatty acids having 20 carbon atoms or more, a salt thereof, and esters other than glycerides can be prepared by known methods using, for example, the glyceride described above as the raw material.

For example, saury crude oil is typically taken by the following method, similar to other fish oils. Whole saury or the processed residues such as fish heads, skins, backbones, and viscera generated by fish processing are crushed, steamed and simmered, and then squeezed to separate them into broth (stickwater, SW) and squeezed meal. The oil and fat obtained together with the broth are separated from the broth by centrifugal separation.

The Standard Tables of Food Composition in Japan, 2015 Version (Seven Revised Edition) describes that fatty acids of saury (with skins, raw) contain 26.0 wt % of docosenoic acid (C22:1), 17.6 wt % of icosenoic acid (C20:1), and the total amount of monounsaturated fatty acids is 54.2 wt %. Saury oil is characterized by having a larger content of monounsaturated fatty acids among fish oils.

The crude oil of fish oil is converted to a refined fish oil by purification steps such as degum, deacid, bleaching, and deodorizing. The refined fish oil can also be used as a source for the ingredient selected from a monounsaturated fatty acid having 20 carbon atoms or more, a salt thereof, and an ester thereof.

In one aspect, an oil having higher concentration of the monounsaturated fatty acid may be used as a source for the ingredient selected from a monounsaturated fatty acid having 20 carbon atoms or more, a salt thereof, and an ester thereof. In this case, an MUFA concentrated triglyceride can be obtained by a method of concentrating using a lipase reaction, or a method of ethyl-esterificating the monounsaturated fatty acid and concentrating the ethyl ester, and then trans-esterifying with glycerin to reconstitute into the triglyceride.

Monounsaturated fatty acids having 20 carbon atoms or more include monounsaturated fatty acids having 20 carbon atoms (C20:1) (for example, C20:1 n-11, C20:1 n-9, and C20:1 n-7), monounsaturated fatty acids having 22 carbon atoms (C22:1) (for example, C22:1 n-11, C22:1 n-9, C22:1 n-7, and C22:1 n-13), and monounsaturated fatty acids having 24 carbon atoms (C24:1) (for example, C24:1 n-9). In a preferred aspect, the active ingredient of the composition for improving sleep according to an embodiment of the present invention is an ingredient selected from C20:1, a salt thereof, and an ester thereof, an ingredient selected from C22:1, a salt thereof, and an ester thereof, or combination thereof.

The content of C22:1 and C20:1 varies depending on the type of fish. Examples of fish with the high content of C22:1 and C20:1 include fish of Scomberesocidae such as saury, fish of Gadidae such as Pacific cod, Alaska pollock, Atlantic cod, and Sablefish, fish of Salmonida such as Chum salmon, Silver salmon, Sockeye salmon, pink salmon, Atlantic Salmon, and Rainbow trout, fish of Osmeriformes such as Capellin and Smelt, and Clupeidae such as Pacific herring. In addition, a relatively large amount of LC-MUFAs is also contained in fish such as Sand lance, tuna, Mackerel, and Alfonsino. A large amount of LC-MUFAs is also contained in liver oil of sharks such as spiny dogfish, basking shark, and silver chimaera. In an embodiment of the present invention, fish oils prepared from these fish can be used as they are, or can be used after purifying or concentrating.

The ratio of the monounsaturated fatty acid having 20 carbon atoms or more to the total fatty acids in the composition for improving sleep according to an embodiment of the present invention is 10 wt % or greater, for example, 11 wt % or greater, 12 wt % or greater, 13 wt % or greater, 14 wt % or greater, 15 wt % or greater, 16 wt % or greater, 17 wt % or greater, 18 wt % or greater, 19 wt % or greater, 20 wt % or greater, 21 wt % or greater, 22 wt % or greater, 23 wt % or greater, 24 wt % or greater, 25 wt % or greater, 26 wt % or greater, 27 wt % or greater, 28 wt % or greater, 29 wt % or greater, 30 wt % or greater, 40 wt % or greater, 50 wt % or greater, 60 wt % or greater, 70 wt % or greater, 80 wt % or greater, or 90 wt % or greater.

Note that, in the present specification, the ratio of the fatty acid to the total fatty acids in the composition (wt %) is calculated by the value measured by gas chromatography after esterifying the ingredient in the composition according to "Manual for Analyzing the Standard Tables of Food Composition in Japan, Five Revised and Enlarged Edition" (the document in Resource Survey Subcommitttee, Science and Technology, and Academic Council, Ministry of Education, Culture, Sports, Science and Technology (2004)). By the content of fatty acids, it also means the ratio of the fatty acid (wt %) to the total fatty acids described above. The analytical conditions used for gas chromatography are listed below.

Instrument: Agilent 6890 GC system (Agilent Technologies)
Column: DB-WAX (Agilent Technologies, 30 m×0.25 mm ID, 0.25 μm film thickness)
Carrier gas: helium (1.0 mL/min, constant flow)
Inlet temperature: 250° C.
Injected quantity of sample: 1 μL
Injection method: split
Split ratio: 20:1
Column oven: 180° C.—3° C./min—230° C.
Detector: FID
Detector temperature: 250° C.

Examples of salts of the monounsaturated fatty acid having 20 carbon atoms or more in an embodiment of the present invention include potassium salts and sodium salts. In addition, examples of esters of the monounsaturated fatty acid having 20 carbon atoms or more include esters of a lower alcohol having 5 carbon atoms or less (for example, methyl esters, ethyl esters, n-propyl esters, i-propyl esters, n-butyl esters, s-butyl esters, t-butyl esters, and n-pentyl esters), esters with glycerin such as monoglycerides, diglycerides, and triglycerides (i.e., glycerides), and phospholipids. In a preferred aspect, the active ingredient of the composition for improving sleep according to an embodiment of the present invention is a glyceride containing a monounsaturated fatty acid having from 20 carbon atoms or more as the constituent fatty acid, and more preferably a triglyceride.

As the monounsaturated fatty acid having from 20 carbon atoms or more in the present invention, oils and fats derived from natural products containing free monounsaturated fatty acids having from 20 carbons or more can be used as they are, or can be used after purifying or concentrating. In addition, as esters of the monounsaturated fatty acid having 20 carbon atoms or more, oils and fats derived from natural products containing monounsaturated fatty acids having from 20 carbon atoms or more as the constituent fatty acid can be used as they are, or can be used after purifying or concentrating.

Furthermore, a fractionated oil obtained by esterifying oils and fats derived from natural products and then fractionating them by high performance liquid chromatography can be used as esters of the monounsaturated fatty acid having 20 carbon atoms or more. Fractionated oils include C20:1 concentrated fractionated oils, C22:1 concentrated fractionated oils, and C24:1 concentrated fractionated oils.

The composition for improving sleep according to an embodiment of the present invention may further include an n-3 polyunsaturated fatty acid and an n-6 polyunsaturated fatty acid. In this case, the area ratio of the n-3 polyunsaturated fatty acid to the n-6 polyunsaturated fatty acid is 4.0 or greater, for example, 5.0 or greater, 6.0 or greater, 7.0 or greater, 8.0 or greater, 9.0 or greater, or 10.0 or greater. In the present specification, the n-3 polyunsaturated fatty acid is a polyunsaturated fatty acid having 18 carbon atoms or more and having two or more carbon-carbon double bonds, and having the first double bond between third and fourth carbon atom, numbering from the carbon of methyl group in the terminal of fatty acid chain. Examples include α-linolenic acid (C18:3 n-3), octadecatetraenoic acid (C18:4 n-3), eicosatetraenoic acid (C20:4 n-3), eicosapentaenoic acid (C20:5 n-3), docosapentaenoic acid (C22:5 n-3), and docosahexaenoic acid (C22:6 n-3). In addition, the n-6 polyunsaturated fatty acid is a polyunsaturated fatty acid having 18 carbon atoms or more and having two or more carbon-carbon double bonds, and having the first double bond between sixth and seventh carbon atom, numbering from the carbon of methyl group in the terminal of fatty acid chain. Examples include linoleic acid (C18:2 n-6), and arachidonic acid (C20:4 n-6). In the present specification, the area ratio of the fatty acid refers to the ratio of the peak area detected by gas chromatography after esterifying the fatty acid in the composition according to AOCS official method Ce1b-89. The analytical conditions used for gas chromatography are listed above.

In an embodiment of the present invention, improving sleep means improving sleep quality, and does not include treatment of sleep disorders, including insomnia and hyperdrosis. Improving sleep includes improving subjective symptoms, for example, improving the mood in morning awake, ease of sleep, and the depth of sleep. In one aspect, the composition for improving sleep according to an embodiment of the present invention is for improving awake.

The subject for administering the composition for improving sleep according to an embodiment of the present invention is a mammal, and preferably a human.

The composition for improving sleep according to an embodiment of the present invention can be prepared in the form suitable for a pharmaceutical composition, a food composition (for example, functional food products, health food products, and supplements), various solid formulations such as a granule (including a dry syrup), a capsule (soft capsule or hard capsule), a tablet (including a chewable tablet), a powder (a powder formulation), and a pill, or liquid formulations such as oral liquid formulations (including a liquid, a suspension, and a syrup). For example, the composition for improving sleep according to an embodiment of the present invention can be formulated as a soft capsule in which a purified fish oil is filled into a gelatin coating.

Examples of additives that help with formulation include excipients, lubricants, binders, disintegrating agents, fluidization agents, dispersing agents, wetting agents, preservatives, thickening agents, pH adjusting agents, colorants, corrigents, surfactants, and solubilization agents. Additionally, prepared as a liquid formulation, thickening agents such as pectin, xanthan gum, guar gum, and the like can be compounded. Moreover, the composition for improving sleep according to an embodiment of the present invention can be formed into a coated tablet formulation by using a coating agent, or be formed into a paste-like gelatin formulation. Furthermore, even when preparing the composition for improving sleep according to an embodiment of the present invention in other forms, it is sufficient to follow known methods.

The composition for improving sleep according to an embodiment of the present invention can take the form of a food composition. In an embodiment of the present invention, the food composition means general food products including beverages. The food composition includes foods for specified health uses and foods with nutrient function defined in the health-promoting food regulations of the Consumer Affairs Agency in addition to general food products including health food products such as supplements. For example, functional food products are provided that have an indication that they have an improved effect on sleep. For example, fish oil-containing food products can be provided as is. The food composition according to an embodiment of the present invention also includes a food material for imparting an improved effect in sleep by adding, mixing or applying to other food products. In addition to food products, it can also be provided as animal feeds or the like.

When the composition for improving sleep according to an embodiment of the present invention is in the form of a food product, the food product is not particularly limited. The food product may be beverages, confectionaries, breads, or soups. Examples include common retort foods, frozen food, ready-to-drink (such as noodles), cans, sausage, cookies, biscuits, cereal bars, crackers, snacks (such as potato chips), pastry, cakes, pies, candies, chewing gum (including pellets and sticks), jellies, soups, ices, dressings, yogurts, or the like, supplements in the form of a tablet, a capsule, and an emulsion, and soft drinks. The method for manufacturing these food products is not particularly limited as long as the effect of the present invention is not impaired, and may be according to the method used by the person skilled in the art for each food products.

It is within the scope of the invention to display the benefits of the composition for improving sleep according to an embodiment of the present invention in packaging containers, product instructions, and brochures and to sell the products according to the present invention. It is also within the scope of the present invention to display the benefits of the present invention on television, Internet websites, brochures, newspaper, magazines, and to advertise and sell the products according to an embodiment of the present invention.

The amount of the ingredient selected from a monounsaturated fatty acid having 20 carbon atoms or more, a salt thereof, and an ester thereof ingested by the subject in an embodiment of the present invention is not particularly limited. For example, the ingredient is ingested in an amount equal to or greater than the effective amount for obtaining the desired effect. Here, the effective amount for obtaining the desired effect refers to the amount required to improve sleep. For example, in the case of an adult, depending on the conditions such as age, weight, and health conditions of the subject, 2 mg/kg weight/day or greater, for example, 3 mg/kg weight/day or greater, 4 mg/kg weight/day or greater, 5 mg/kg weight/day or greater, 6 mg/kg weight/day or greater, 7 mg/kg weight/day or greater, 8 mg/kg weight/day or greater, 9 mg/kg weight/day or greater, 10 mg/kg weight/day or greater, 11 mg/kg weight/day or greater, 12 mg/kg weight/day or greater, 13 mg/kg weight/day or greater, 14 mg/kg weight/day or greater, 15 mg/kg weight/day or greater, 16 mg/kg weight/day or greater, 17 mg/kg weight/day or greater, 18 mg/kg weight/day or greater, 19 mg/kg weight/day or greater, 20 mg/kg weight/day or greater, 21 mg/kg weight/day or greater, 22 mg/kg weight/day or greater, 23 mg/kg weight/day or greater, 24 mg/kg weight/day or greater, 25 mg/kg weight/day or greater, 30 mg/kg weight/day or greater, 40 mg/kg weight/day or greater, 50 mg/kg weight/day or greater, 100 mg/kg weight/day or greater, or 200 mg/kg weight/day or greater of the active ingredient based on the monounsaturated fatty acid having 20 carbon atoms or more can be ingested for 4 weeks or more, for example, 5 weeks or more, 6 weeks or more, 7 weeks or more, 8 weeks or more, 9 weeks or more, 10 weeks or more, 11 weeks or more, 12 weeks or more. In addition, since the ingredient selected from a monounsaturated fatty acid having 20 carbon atoms or more, a salt thereof does not have a strong side effect, there is no restriction on the daily amount of ingestion.

EXAMPLES

The present invention is described specifically below by citing Examples, but the present invention is not limited to these Examples.

Note that in the Examples, the value represented in % is wt %, unless otherwise indicated.

(Example 1) Intervention Study 1

(1) Test Method a) Test Food Product: the capsule containing 0.35 g of fish oils derived from saury (containing about 29% of LC-MUFA to all fatty acids (27 wt % to the total weight of the fish oils) and the can of baked saury with salt (commercially available from Nippon Suisan Kaisha, Ltd.).

Fatty acid compositions of purified saury oil in the capsule and the can of baked saury with salt are shown in Table 1. The fatty acid composition of the purified saury oil was calculated by the value measured by gas chromatography after esterifying the ingredient in the composition according to AOCS official method Ce1b-89. The fatty acid composition of the can of baked saury with salt is the result of analysis by the Japan Food Research Laboratories. The analytical conditions for gas chromatography according to AOCS official method Ce1b-89 are listed below.

Instrument: Agilent 6890 GC system (Agilent Technologies)

Column: DB-WAX (Agilent Technologies, 30 m×0.25 mm ID, 0.25 μm film thickness)

Carrier gas: helium (1.0 mL/min, constant flow)

Inlet temperature: 250° C.

Injected quantity of sample: 1 μL

Injection method: split

Split ratio: 20:1

Column oven: 180° C.—3° C./min—230° C.

Detector: FID

Detector temperature: 250° C.

TABLE 1

| | Can of baked saury with salt | | Purified saury oil |
|---|---|---|---|
| | Fatty acid | | (Lot. 120823) |
| | composition (%) | | Fatty acid composition |
| Fatty acid | Broth | Solid | Fatty acid | (%) |
| C14:0 | 6.1 | 5.7 | C14:0 | 6.7 |
| C16:0 | 9.9 | 10.7 | C16:0 | 11.2 |
| C16:1n7 | 3.0 | 2.9 | C16:1n-7 | 2.7 |
| C18:0 | 1.6 | 1.9 | C18:0 | 1.7 |
| C18:1n9 | 5.0 | 4.7 | C18:1n-9 | 5.2 |
| C18:1n7 | 1.0 | 1.0 | C18:1n-7 | 1.0 |
| C18:2n6 | 1.6 | 1.4 | C18:2n-6 | 1.7 |
| C18:3n3 | 1.4 | 1.2 | C18:3n-3 | 1.6 |
| C18:4n3 | 4.7 | 4.2 | C18:4n-3 | 5.9 |
| C20:0 | 0.2 | 0.2 | C20:0 | 0.2 |
| C20:1n11 | 13.3 | 12.4 | C20:1n-11 | 10.3 |
| C20:1n9 | 2.7 | 2.8 | C20:1n-9 | 2.7 |
| C20:1n7 | 0.2 | 0.2 | C20:1n-7 | 0.2 |
| C20:4n6 | 0.4 | 0.5 | C20:4n-6 | 0.6 |
| C20:4n3 | 1.1 | 1.0 | C20:4n-3 | 1.2 |
| C20:5n3 | 7.1 | 6.3 | C20:5n-3 | 6.3 |
| C22:1n11 | 17.7 | 17.2 | C22:1n-11 | 15.4 |
| C22:1n9 | 0.7 | 0.7 | C22:1n-9 | 0.6 |
| C22:1n7 | 0.2 | 0.2 | C22:1n-7 | 0.2 |
| C22:5n3 | 1.5 | 1.5 | C22:5n-3 | 1.3 |
| C22:6n3 | 12.3 | 15.0 | C22:6n-3 | 11.8 |
| C24:0 | 0.9 | 0.9 | others | 11.6 |
| others | 7.7 | 7.5 | LCMUFA | 29.4 |
| LCMUFA | 34.6 | 33.5 | EPA + DHA + DPA | 19.4 |
| EPA + DHA + DPA | 20.9 | 22.8 | | |

The general ingredient table and fatty acid contents of the capsule of saury oil are shown in Table 2. The general ingredient table and fatty acid contents of the can of baked saury with salt are shown in Table 3. Analytical results (acid value, peroxide value, p-anisidine value, and lipid composition) of the purified saury oil in the capsules are shown in Table 4.

TABLE 2

| <Capsule of saury oil> General ingredient table (per 12 capsules) | |
|---|---|
| Calorie | 45 kcal |
| Protein | 1.4 g |
| Lipid | 4.2 g |
| Carbohydrate | 0.2 g |
| Sodium | 1.1 mg |

| | Fatty acid composition (%) | per 12 capsules |
|---|---|---|
| C20:1 | 13.2 | 518 mg |
| C22:1 | 16.2 | 635 mg |
| EPA | 6.3 | 246 mg |
| DHA | 11.8 | 449 mg |
| LC-MUFA | 29.4 | 1153 mg |
| EPA + DHA | 18.1 | 695 mg |

TABLE 3

| <Can of baked saury with salt> General ingredient table (per one 75-g can) | |
|---|---|
| Moisture | 44 g |
| Protein | 14.9 g |
| Lipid | 14.6 g |
| Carbohydrate | 0 g |
| Ash | 1.5 g |
| Calorie | 191 kcal |

TABLE 3-continued

<Can of baked saury with salt>
General ingredient table (per one 75-g can)

| Sodium | 214 mg |
|---|---|
| Salt equivalent (expressed as sodium) | 0.7 g |

Fatty acid composition and content in solid

| | Fatty acid composition (%) | Content (g/can) |
|---|---|---|
| C20:1 | 15.4 | 2.25 |
| C22:1 | 18.1 | 2.64 |
| EPA | 6.3 | 0.92 |
| DHA | 15 | 2.19 |
| LC-MUFA | 33.5 | 4.89 |
| EPA + DHA | 21.3 | 3.11 |

TABLE 4

Analytical results of the saury oil
[Sample]
Sample 1. Purified saury oil (Lot. 120823)

[Analyzing items]

| Items | Analyzing method |
|---|---|
| Acid value | Ph. Eur. |
| Peroxide value | Ph. Eur. |
| p-anisidine value | Ph. Eur. |
| Lipid composition | TLC-FID |

[Result of analysis]

| Analyzing items | Sample 1 |
|---|---|
| Acid value | 0.03 |
| Peroxide value | 0.6 meq/kg |
| p-anisidine value | 6.8 |
| Lipid composition | |
| TAG | 98.0% |
| FFA | 0.0% |
| DAG | 2.0% |
| MAG | 0.0% |
| PL | 0.0% | b) Subjects: 49 healthy adult individuals including students of the Tokushima University having age of 20 or more were divided two groups (a capsule ingestion group and a can ingestion group). As the capsule ingestion group, 24 individuals having age of 22 in average (average weight: 53.2 kg (before ingestion) and 52.9 kg (after ingestion)) were participated in. As the can ingestion group, 25 individuals having age of 21 in average (average weight: 53.3 kg (before ingestion) and 53.0 kg (after ingestion)) were participated in (Tables 7-1 and 7-2). During the study, one individual of the capsule ingestion group stopped the test because neutral fat showed high value, and one individual in the can ingestion group was excluded because of the violation of the intake criteria.

c) Test condition: the capsule ingestion group ingested 12 capsules per day for 4 weeks. The can ingestion group ingested at a rate of 4 cans per a week for a total of 4 weeks. The 12 capsules contained 4.2 g of saury oil. The subjects would ingest about 1.1 gas LC-MUFA per day. The can of baked saury with salt contained about 15 g of oils and fats per one can (75 g). The subjects would ingest about 4.9 g as LC-MUFA per day.

Blood test and biochemistry tests, QOL questionnaires, and vascular endothelial function measurements were taken before the start of the study and at 4 weeks after ingestion.

Blood test and biochemistry tests were performed on SRL Corporation.

QOL questionnaires were conducted with VAS (visual analogue scale) for six questionnaires (fasting, swell, fatigue, wakefulness, tasty, and enjoyment). Subjects answered their current states in the rate of 0 to 100 for each questionnaire. For example, for wakefulness, it is a relative quantified evaluation of the mood upon wake-up of the subject when the condition in which the subject can wake up comfortably in the morning is taken as 100, and the condition in which the subject can not wake up comfortably at all is taken as 0. Higher values indicate the improvement of awake.

Vascular endothelial function was evaluated by measuring FMD values using a Flow Mediated Dilation (FMD) test device UNEX EF (manufactured by UNEX corporation). The FMD Value (%) was calculated by maximum expanded width (mm)/resting vessel diameter (mm)×100.

Statistical software Graphpad Prism (from MDF Co., Ltd.) was used for statistical processing. Multiple groups of tests were performed using a one-way variance analysis method, and a Tukey's multiple comparisons test was used for the multiple comparison test. For intergroup comparison between two groups, unpaired t-test which is an independent comparison of two groups was used. For intragroup comparison, paired t-test which is a dependent comparison of two groups was used.

d) Run time: From Apr. 5, 2016 to Jun. 30, 2016

(2) Test Results (2-1) FMD Test

Figures 1, 2:
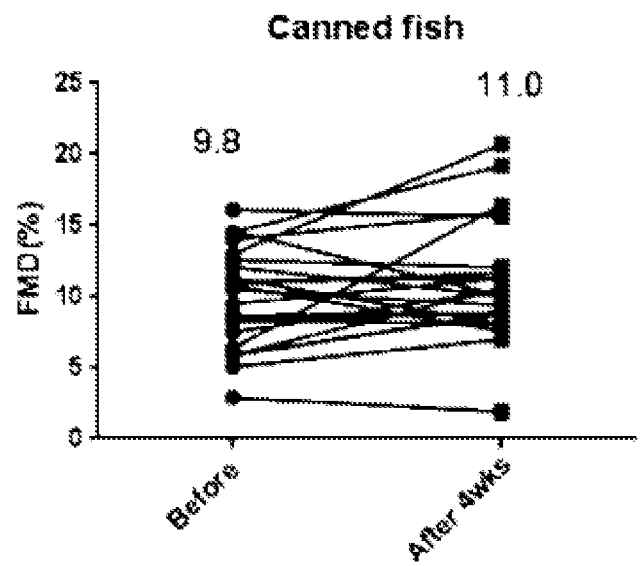
Figures 1, 2, 3:
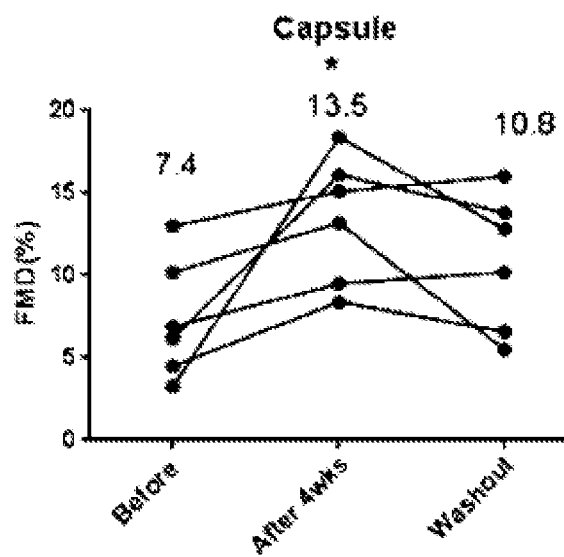

As shown in Table 5 and FIGS. 1-1 and 1-2, significant improvement of FMD values was observed for both groups compared to before ingestion and at 4 weeks after the start of ingestion of the capsule or the can. The improvement in FMD value of about 44% was observed in the capsule ingestion group. The improvement in FMD value of about 12% was observed in the can ingestion group.

TABLE 5

Individual data representing changes in FMD values of subjects before and after ingestion in the capsule group and the can group

| ID | Before ingestion | After ingestion | After washout |
|---|---|---|---|
| Capsule group | | | |
| 1 | 10.2 | 13.2 | 5.5 |
| 2 | 3.3 | 18.4 | 12.8 |
| 3 | 4.5 | 8.4 | 6.6 |
| 4 | 13.5 | 17.1 | n.t. |
| 5 | 6.9 | 9.5 | 10.2 |
| 6 | 8.3 | 15.3 | n.t. |
| 7 | 13 | 15.1 | 16 |
| 8 | 6.2 | 16.1 | 13.8 |
| 9 | 9.1 | 10.3 | n.t. |
| 10 | 8.4 | 10.8 | n.t. |
| 11 | 5 | 10.9 | n.t. |

TABLE 5-continued

Individual data representing changes in FMD values of subjects before and after ingestion in the capsule group and the can group

| ID | Before ingestion | After ingestion | After washout |
|---|---|---|---|
| 12 | 7.4 | 9.7 | n.t. |
| 13 | 16.6 | 16 | n.t. |
| 14 | 11.9 | 11.9 | n.t. |
| 15 | 6 | 10.9 | n.t. |
| 16 | 7.3 | 6.1 | n.t. |
| 17 | 12.3 | 19.9 | n.t. |
| 18 | 10.1 | 6.6 | n.t. |
| 19 | 4.3 | 5.8 | n.t. |
| 20 | 8.7 | 16 | n.t. |
| 21 | 8.6 | 12.8 | n.t. |
| 22 | 6.3 | 6.3 | n.t. |
| 23 | 8.1 | 12.9 | n.t. |
| av | 8.5 | 12.2 | |
| Can group | | | |
| 24 | 14.5 | 19.2 | n.t. |
| 25 | 13 | 20.7 | 14.3 |
| 26 | 2.9 | 1.9 | n.t. |
| 27 | 10.9 | 11.7 | n.t. |
| 28 | 10.5 | 9.4 | n.t. |
| 29 | 8.7 | 8.8 | n.t. |
| 30 | 14 | 15.9 | n.t. |
| 31 | 8.4 | 8.1 | n.t. |
| 32 | 12.6 | 12.1 | n.t. |
| 33 | 6.4 | 16.4 | 10.1 |
| 34 | 5.1 | 7 | n.t. |
| 35 | 8.3 | 8.9 | 13.1 |
| 36 | 11.1 | 11.3 | n.t. |
| 37 | 10.8 | 7.6 | n.t. |
| 38 | 16.1 | 15.6 | n.t. |
| 39 | 7.5 | 10.5 | n.t. |
| 40 | 5.9 | 8.8 | n.t. |
| 41 | 5.9 | 10.6 | n.t. |
| 42 | 12.1 | 10.1 | n.t. |
| 43 | 14.6 | 10.1 | n.t. |
| 44 | 5.9 | 8.8 | n.t. |
| 45 | 9.5 | 11.3 | n.t. |
| 46 | 11.3 | 8.1 | n.t. |
| av | 9.8 | 11.0 | | av: Average value;
n.t.: Not tested

In addition, for nine subjects in which the increase of FMD value was observed, the FMD value was measured again by providing a washout period of 4 weeks after the end of ingestion. As a result, as illustrated in FIGS. 1-3 and 1-4, a tendency was observed in which the FMD value declined after the washout period. This confirmed that the ingestion of fish oil likely increased the FMD value.

In addition, when data was analyzed for subjects having FMD values of less than 6% before ingestion and suspected vascular endothelial disorder, both groups tended to increase FMD values after ingestion. This suggests that the ingestion of saury oil may not only increase vascular endothelial function in subjects with FMD values within normal range, but also improve vascular endothelial disorders in subjects with FMD values outside of normal range. Also, since the saury oil is enriched in LC-MUFA, the possibility that LC-MUFA influences vascular endothelium and improves vascular endothelial function was shown.

(2-2) QOL Questionnaires

As shown in Tables 6-1 and 6-2 and FIG. 2, awaking was improved in the capsule group.

TABLE 6-1

Individual data representing results of QOL questionnaires before and after ingestion of subjects in capsule group

| | Capsule group | | | | | | | | | | | |
|---|---|---|---|---|---|---|---|---|---|---|---|---|
| | Fasting | | Swell | | Fatigue | | Wakefulness | | Tastiness | | Enjoyment | |
| ID | Before ingestion | After ingestion | Before ingestion | After ingestion | Before ingestion | After ingestion | Before ingestion | After ingestion | Before ingestion | After ingestion | Before ingestion | After ingestion |
| 1 | 88 | 48 | 49 | 59 | 10 | 30 | 41 | 31 | 97 | 100 | 97 | 100 |
| 2 | 87 | 81 | 18 | 32 | 40 | 8 | 6 | 72 | 100 | 100 | 100 | 100 |
| 3 | 24 | 62 | 82 | 23 | 72 | 25 | 23 | 75 | 92 | 93 | 92 | 93 |
| 4 | 81 | 23 | 30 | 49 | 14 | 90 | 81 | 99 | 99 | 100 | 93 | 100 |
| 5 | 21 | 0 | 70 | 100 | 18 | 85 | 15 | 31 | 100 | 100 | 99 | 100 |
| 6 | 51 | 44 | 83 | 44 | 84 | 46 | 17 | 80 | 86 | 15 | 100 | 15 |
| 7 | 13 | 98 | 86 | 97 | 46 | 75 | 32 | 100 | 100 | 98 | 100 | 99 |
| 8 | 50 | 45 | 78 | 94 | 35 | 20 | 35 | 19 | 87 | 84 | 89 | 85 |
| 9 | 79 | 49 | 14 | 29 | 58 | 22 | 74 | 77 | 79 | 77 | 80 | 79 |
| 10 | 58 | 80 | 9 | 50 | 31 | 55 | 19 | 69 | 89 | 91 | 99 | 97 |
| 11 | 91 | 78 | 89 | 41 | 25 | 74 | 48 | 30 | 95 | 94 | 98 | 97 |
| 12 | 42 | 36 | 15 | 50 | 15 | 29 | 17 | 16 | 80 | 69 | 81 | 90 |
| 13 | 21 | 49 | 78 | 42 | 34 | 42 | 48 | 40 | 98 | 60 | 98 | 60 |
| 14 | 14 | 100 | 100 | 100 | 79 | 100 | 80 | 85 | 100 | 100 | 100 | 100 |
| 15 | 45 | 42 | 53 | 63 | 56 | 52 | 77 | 44 | 99 | 86 | 99 | 87 |
| 16 | 78 | 83 | 19 | 94 | 63 | 52 | 96 | 95 | 95 | 96 | 96 | 96 |
| 17 | 48 | 91 | 90 | 45 | 71 | 93 | 95 | 94 | 95 | 94 | 70 | 68 |
| 18 | 37 | 86 | 61 | 85 | 60 | 65 | 93 | 76 | 100 | 100 | 100 | 100 |
| 19 | 39 | 60 | 37 | 36 | 43 | 44 | 19 | 33 | 86 | 74 | 84 | 91 |
| 20 | 35 | 49 | 50 | 49 | 50 | 50 | 30 | 28 | 65 | 50 | 76 | 81 |
| 21 | 20 | 47 | 2 | 47 | 47 | 63 | 30 | 79 | 96 | 99 | 98 | 99 |
| 22 | 9 | 82 | 100 | 0 | 24 | 83 | 33 | 61 | 100 | 100 | 100 | 100 |
| 23 | 30 | 65 | 61 | 63 | 20 | 37 | 60 | 47 | 67 | 77 | 78 | 82 |

TABLE 6-2

Individual data representing results of QOL questionnaires before and after ingestion of subjects in can group

| | Can | | | | | | | | | | | |
|---|---|---|---|---|---|---|---|---|---|---|---|---|
| | Fasting | | Swell | | Fatigue | | Wakefulness | | Tastiness | | Enjoyment | |
| ID | Before | After | Before | After | Before | After | Before | After | Before | After | Before | After |
| 24 | 78 | 72 | 99 | 50 | 74 | 50 | 98 | 50 | 99 | 99 | 99 | 99 |
| 25 | 79 | 70 | 45 | 74 | 42 | 45 | 26 | 34 | 92 | 91 | 94 | 91 |
| 26 | 23 | 41 | 22 | 40 | 51 | 49 | 77 | 88 | 76 | 70 | 61 | 70 |
| 27 | 89 | 77 | 92 | 92 | 91 | 83 | 95 | 84 | 100 | 95 | 100 | 96 |
| 28 | 21 | 31 | 45 | 59 | 36 | 31 | 34 | 88 | 73 | 88 | 73 | 87 |
| 29 | 51 | 12 | 19 | 74 | 68 | 47 | 46 | 48 | 86 | 72 | 84 | 77 |
| 30 | 10 | 27 | 48 | 19 | 1 | 21 | 29 | 68 | 100 | 100 | 100 | 100 |
| 31 | 96 | 19 | 91 | 92 | 51 | 17 | 74 | 63 | 99 | 100 | 99 | 100 |
| 32 | 49 | 49 | 97 | 28 | 3 | 25 | 12 | 25 | 96 | 98 | 98 | 85 |
| 33 | 80 | 79 | 56 | 67 | 63 | 77 | 93 | 88 | 90 | 85 | 91 | 86 |
| 34 | 21 | 30 | 21 | 6 | 78 | 47 | 77 | 82 | 80 | 39 | 90 | 61 |
| 35 | 47 | 45 | 49 | 88 | 39 | 34 | 50 | 60 | 77 | 60 | 79 | 82 |
| 36 | 50 | 81 | 83 | 82 | 27 | 72 | 84 | 83 | 96 | 96 | 97 | 97 |
| 37 | 89 | 78 | 85 | 21 | 50 | 22 | 11 | 19 | 95 | 89 | 96 | 87 |
| 38 | 86 | 24 | 47 | 77 | 72 | 46 | 97 | 47 | 98 | 95 | 98 | 96 |
| 39 | 97 | 99 | 97 | 97 | 74 | 96 | 98 | 96 | 97 | 97 | 95 | 98 |
| 40 | 81 | 73 | 26 | 72 | 48 | 87 | 98 | 99 | 97 | 97 | 96 | 96 |
| 41 | 27 | 68 | 88 | 22 | 40 | 66 | 20 | 76 | 94 | 91 | 98 | 93 |
| 42 | 21 | 22 | 62 | 37 | 23 | 67 | 93 | 79 | 93 | 78 | 91 | 86 |
| 43 | 72 | 80 | 22 | 59 | 42 | 61 | 75 | 85 | 100 | 81 | 100 | 100 |
| 44 | 85 | 79 | 92 | 97 | 71 | 91 | 63 | 56 | 100 | 100 | 100 | 100 |
| 45 | 100 | 22 | 56 | 15 | 52 | 88 | 52 | 50 | 82 | 87 | 82 | 87 |
| 46 | 95 | 90 | 95 | 90 | 52 | 8 | 92 | 66 | 94 | 65 | 94 | 68 |
| 47 | 33 | 64 | 53 | 63 | 57 | 22 | 67 | 63 | 100 | 99 | 100 | 99 |

(2-3) Body Composition Measurement

Body composition evaluations (weight, body fat, fat removal mass, muscle mass, body moisture content, and BMI) were measured using a Dual Frequency Total Body Composition Analyzer (DC—320, available from TANITA corporation). As shown in Tables 7-1 and 7-2 and FIG. 3, the capsule group significantly reduced body fat percentage.

TABLE 7-1

Individual data representing changes in body composition of subjects before and after ingestion in capsule group

| | Age (year-old) | | Height (cm) | | Weight (kg) | | Body fat percentage (%) | | Fat mass (kg) | |
|---|---|---|---|---|---|---|---|---|---|---|
| ID | Before ingestion | After ingestion | Before ingestion | After ingestion | Before ingestion | After ingestion | Before ingestion | After ingestion | Before ingestion | After ingestion |
| 1 | 21 | 21 | 161.0 | 161.0 | 51.4 | 50.5 | 27.7 | 27.4 | 14.2 | 13.8 |
| 2 | 21 | 21 | 156.0 | 156.0 | 50.1 | 50.1 | 31 | 32.2 | 15.5 | 16.1 |
| 3 | 21 | 21 | 166.0 | 166.0 | 47 | 47.1 | 23.7 | 24.5 | 11.1 | 11.5 |
| 4 | 20 | 20 | 168.0 | 168.0 | 47.5 | 46.9 | 23.9 | 23.7 | 11.4 | 11.1 |
| 5 | 24 | 24 | 165.2 | 165.0 | 64.3 | 64.3 | 36 | 35.3 | 23.1 | 22.7 |
| 6 | 20 | 20 | 173.0 | 173.8 | 69 | 70.0 | 18.7 | 18.3 | 12.9 | 12.8 |
| 7 | 23 | 23 | 164.5 | 164.7 | 54.1 | 53.7 | 25.8 | 23.7 | 14 | 12.7 |
| 8 | 22 | 22 | 153.0 | 153.0 | 42.2 | 42.6 | 22.1 | 21.3 | 9.3 | 9.1 |
| 9 | 21 | 22 | 159.0 | 159.0 | 60.1 | 61.9 | 32.8 | 33.2 | 19.7 | 20.6 |
| 10 | 20 | 20 | 157.0 | 157.0 | 46.8 | 46.5 | 27.6 | 26.6 | 12.9 | 12.4 |
| 11 | 20 | 21 | 166.0 | 166.0 | 55.1 | 54.7 | 28.1 | 26.4 | 15.5 | 14.4 |
| 12 | 20 | 20 | 163.4 | 163.4 | 57.7 | 57.2 | 29 | 28.4 | 16.7 | 16.2 |
| 13 | 21 | 21 | 157.5 | 157.5 | 50.6 | 49.6 | 29.1 | 28.2 | 14.7 | 14 |
| 14 | 22 | 22 | 163.0 | 163.5 | 49 | 48.2 | 22.3 | 22 | 10.9 | 10.6 |
| 15 | 21 | 21 | 170.8 | 170.8 | 61.5 | 62.3 | 12.9 | 14.2 | 7.9 | 8.8 |
| 16 | 33 | 33 | 168.0 | 168.0 | 56.2 | 54.5 | 26.6 | 25.8 | 14.9 | 14.1 |
| 17 | 20 | 20 | 161.8 | 161.8 | 54.4 | 54.0 | 29.1 | 27.4 | 15.8 | 14.8 |
| 18 | 22 | 22 | 159.5 | 159.5 | 45.3 | 44.5 | 22.6 | 20.9 | 10.2 | 9.3 |
| 19 | 22 | 22 | 161.0 | 161.0 | 50.5 | 50.4 | 28 | 27.6 | 14.1 | 13.9 |
| 20 | 21 | 21 | 153.0 | 153.0 | 50.6 | 49.3 | 31 | 30 | 15.7 | 14.8 |
| 21 | 20 | 21 | 160.4 | 160.4 | 52.3 | 52.2 | 28.9 | 28.6 | 15.1 | 14.9 |
| 22 | 20 | 20 | 169.0 | 169.0 | 54.3 | 54.5 | 30.6 | 29.3 | 16.6 | 16 |
| 23 | 20 | 20 | 148.5 | 148.5 | 53.4 | 51.1 | 39.4 | 35.6 | 21 | 18.2 |

TABLE 7-1-continued

Individual data representing changes in body composition of subjects before and after ingestion in capsule group

| ID | Fat removal mass (kg) Before ingestion | Fat removal mass (kg) After ingestion | Muscle mass (kg) Before ingestion | Muscle mass (kg) After ingestion | Body moisture content (kg) Before ingestion | Body moisture content (kg) After ingestion | BMI Before ingestion | BMI After ingestion |
|---|---|---|---|---|---|---|---|---|
| 1 | 37.2 | 36.7 | 35.1 | 34.6 | 25.4 | 24.7 | 19.8 | 19.5 |
| 2 | 34.6 | 34 | 32.7 | 32.2 | 24.1 | 23.6 | 20.6 | 20.6 |
| 3 | 35.9 | 35.6 | 33.9 | 33.6 | 23 | 22.7 | 17.1 | 17.1 |
| 4 | 36.1 | 35.8 | 34.1 | 33.8 | 22.8 | 22.6 | 16.8 | 16.6 |
| 5 | 41.2 | 41.6 | 38.8 | 39.1 | 27.7 | 28.7 | 23.6 | 23.6 |
| 6 | 56.1 | 57.2 | 53.2 | 54.2 | 38.4 | 39.6 | 23.1 | 23.2 |
| 7 | 40.1 | 41 | 37.8 | 38.6 | 27.7 | 28.4 | 20 | 19.8 |
| 8 | 32.9 | 33.5 | 31.2 | 31.7 | 22.8 | 23.3 | 18 | 18.2 |
| 9 | 40.4 | 41.3 | 38 | 38.9 | 29.3 | 30.9 | 23.8 | 24.5 |
| 10 | 33.9 | 34.1 | 32.1 | 32.3 | 22.9 | 23.3 | 19 | 18.9 |
| 11 | 39.6 | 40.3 | 37.3 | 37.9 | 26.8 | 27.3 | 20 | 19.9 |
| 12 | 41 | 41 | 38.6 | 38.6 | 28.8 | 28.9 | 21.6 | 21.4 |
| 13 | 35.9 | 35.6 | 33.9 | 33.6 | 24.9 | 24.6 | 20.4 | 20 |
| 14 | 38.1 | 37.6 | 35.9 | 35.5 | 25.7 | 25.3 | 18.4 | 18 |
| 15 | 53.6 | 53.5 | 50.8 | 50.7 | 36.7 | 36.8 | 21.1 | 21.4 |
| 16 | 41.3 | 40.4 | 38.9 | 38 | 27.7 | 27.2 | 19.9 | 19.3 |
| 17 | 38.6 | 39.2 | 36.4 | 36.9 | 26.8 | 27.5 | 20.8 | 20.6 |
| 18 | 35.1 | 35.2 | 33.2 | 33.3 | 23.7 | 23.8 | 17.8 | 17.5 |
| 19 | 36.4 | 36.5 | 34.4 | 34.5 | 24.5 | 24.6 | 19.5 | 19.4 |
| 20 | 34.9 | 34.5 | 33 | 32.6 | 25 | 24.5 | 21.6 | 21.1 |
| 21 | 37.2 | 37.3 | 35.1 | 35.2 | 25.6 | 25.8 | 20.3 | 20.3 |
| 22 | 37.7 | 38.5 | 35.6 | 36.3 | 24 | 24.7 | 19 | 19.1 |
| 23 | 32.4 | 32.9 | 30.7 | 31.2 | 22.4 | 23.8 | 24.2 | 23.2 |

TABLE 7-2

Individual data representing changes in body composition of subjects before and after ingestion in can group

| ID | Age(year-old) Before ingestion | Age(year-old) After ingestion | Height (cm) Before ingestion | Height (cm) After ingestion | Weight (kg) Before ingestion | Weight (kg) After ingestion | Body fat percentage (%) Before ingestion | Body fat percentage (%) After ingestion | Fat mass (kg) Before ingestion | Fat mass (kg) After ingestion |
|---|---|---|---|---|---|---|---|---|---|---|
| 24 | 25 | 25 | 149.0 | 148.5 | 54.9 | 54.8 | 36 | 36.5 | 19.8 | 20 |
| 25 | 21 | 21 | 152.0 | 152.0 | 46 | 45.9 | 27.5 | 27.2 | 12.6 | 12.5 |
| 26 | 20 | 21 | 160.0 | 161.0 | 60.8 | 60.6 | 32.7 | 33 | 19.9 | 20 |
| 27 | 20 | 20 | 156.0 | 156.6 | 67.1 | 66.7 | 38 | 37.4 | 25.5 | 24.9 |
| 28 | 21 | 21 | 173.0 | 173.0 | 79.3 | 78.3 | 21.5 | 21.8 | 17 | 17.1 |
| 29 | 20 | 20 | 160.0 | 160.0 | 63.7 | 64.8 | 35.8 | 36.1 | 22.8 | 23.4 |
| 30 | 20 | 21 | 156.5 | 156.5 | 53.3 | 53.5 | 33.5 | 34.1 | 17.9 | 18.2 |
| 31 | 20 | 20 | 167.7 | 167.0 | 62.7 | 63.4 | 17.1 | 17.9 | 10.7 | 11.3 |
| 32 | 20 | 20 | 170.0 | 169.0 | 53.9 | 54.9 | 23.3 | 25.1 | 12.6 | 13.8 |
| 33 | 20 | 20 | 163.0 | 163.0 | 56 | 58.6 | 25.7 | 27.2 | 14.4 | 15.9 |
| 34 | 21 | 21 | 151.0 | 151.0 | 44.3 | 43.5 | 23.6 | 22.4 | 10.5 | 9.7 |
| 35 | 20 | 20 | 168.0 | 169.0 | 55.7 | 53.7 | 12.5 | 11.1 | 7 | 6 |
| 36 | 24 | 24 | 171.0 | 171.0 | 69.5 | 70.1 | 19.6 | 20.3 | 13.6 | 14.2 |
| 37 | 20 | 20 | 161.3 | 161.5 | 51.8 | 51 | 29.6 | 29.2 | 15.3 | 14.9 |
| 38 | 20 | 21 | 157.2 | 156.2 | 44.3 | 42.7 | 21.7 | 20.1 | 9.6 | 8.6 |
| 39 | 20 | 20 | 149.0 | 149.0 | 46 | 44.9 | 27.3 | 25 | 12.6 | 11.2 |
| 40 | 20 | 20 | 160.0 | 160.0 | 43.7 | 43 | 12.3 | 12 | 5.4 | 5.2 |
| 41 | 20 | 20 | 160.0 | 160.0 | 51.4 | 51.9 | 16.4 | 17.6 | 8.4 | 9.1 |
| 42 | 20 | 20 | 161.0 | 161.0 | 56.2 | 57.4 | 24.9 | 25.7 | 14 | 14.8 |
| 43 | 21 | 21 | 160.0 | 160.0 | 50 | 49.8 | 25.4 | 23.4 | 12.7 | 11.7 |
| 44 | 20 | 20 | 157.0 | 157.0 | 52.6 | 52.9 | 26.9 | 26.9 | 14.1 | 14.2 |
| 45 | 20 | 20 | 153.3 | 153.3 | 53.2 | 52.5 | 32.5 | 32.3 | 17.3 | 17 |
| 46 | 20 | 20 | 161.0 | 161.0 | 53.7 | 52.3 | 24.5 | 24.1 | 13.2 | 12.6 |
| 47 | 20 | 20 | 164.9 | 164.9 | 58.7 | 57.7 | 29.3 | 27.6 | 17.2 | 15.9 |

| ID | Fat removal mass (kg) Before ingestion | Fat removal mass (kg) After ingestion | Muscle mass (kg) Before ingestion | Muscle mass (kg) After ingestion | Body moisture content (kg) Before ingestion | Body moisture content (kg) After ingestion | BMI Before ingestion | BMI After ingestion |
|---|---|---|---|---|---|---|---|---|
| 24 | 35.1 | 34.8 | 33.2 | 32.9 | 26.5 | 26.3 | 24.7 | 24.9 |
| 25 | 33.4 | 33.4 | 31.6 | 31.6 | 23.5 | 23.6 | 19.9 | 19.9 |
| 26 | 40.9 | 40.6 | 38.5 | 38.2 | 29.7 | 29.3 | 23.8 | 23.4 |
| 27 | 41.6 | 41.8 | 39.1 | 39.3 | 32.7 | 32.7 | 27.6 | 27.2 |

TABLE 7-2-continued

Individual data representing changes in body composition of subjects before and after ingestion in can group

| 28 | 62.3 | 61.2 | 59.1 | 58   | 45.1 | 43.7 | 26.5 | 26.2 |
|----|------|------|------|------|------|------|------|------|
| 29 | 40.9 | 41.4 | 38.5 | 38.9 | 29.9 | 30.6 | 24.9 | 25.3 |
| 30 | 35.4 | 35.3 | 33.5 | 33.4 | 25   | 23.6 | 21.8 | 21.8 |
| 31 | 52   | 52.1 | 49.3 | 49.4 | 35.6 | 35.7 | 22.3 | 22.7 |
| 32 | 41.3 | 41.1 | 38.9 | 38.7 | 27.5 | 27.6 | 18.7 | 19.2 |
| 33 | 41.6 | 42.7 | 39.1 | 40.1 | 29.2 | 31   | 21.1 | 22.1. |
| 34 | 33.8 | 33.8 | 32   | 32   | 24.1 | 24.1 | 19.4 | 19.1 |
| 35 | 48.7 | 47.7 | 46.2 | 45.2 | 33.1 | 31.8 | 19.7 | 18.8 |
| 36 | 55.9 | 55.9 | 53   | 53   | 39   | 38.8 | 23.8 | 24   |
| 37 | 36.5 | 36.1 | 34.5 | 34.1 | 24.6 | 24.2 | 19.9 | 19.6 |
| 38 | 34.7 | 34.1 | 32.8 | 32.3 | 23.7 | 23.3 | 17.9 | 17.5 |
| 39 | 33.4 | 33.7 | 31.6 | 31.9 | 24.2 | 24.3 | 20.7 | 20.2 |
| 40 | 38.3 | 37.8 | 36.1 | 35.7 | 26   | 25.7 | 17.1 | 16.8 |
| 41 | 43   | 42.8 | 40.4 | 40.2 | 30.2 | 30.9 | 20.1 | 20.3 |
| 42 | 42.2 | 42.6 | 39.7 | 40   | 30.6 | 31.6 | 21.7 | 22.1 |
| 43 | 37.3 | 38.1 | 35.2 | 35.9 | 25.8 | 26.5 | 19.5 | 19.5 |
| 44 | 38.5 | 38.7 | 36.3 | 36.5 | 27.6 | 28   | 21.3 | 21.5 |
| 45 | 35.9 | 35.5 | 33.9 | 33.6 | 26.1 | 25.7 | 22.6 | 22.3 |
| 46 | 40.5 | 39.7 | 38.1 | 37.4 | 28.8 | 27.7 | 20.7 | 20.2 |
| 47 | 41.5 | 41.8 | 39   | 39.3 | 29.2 | 29.3 | 21.6 | 21.2 |

(2-4) Blood Test, Blood Biochemistry Test

No abnormalities were observed in both groups in the blood test (Table 8). Blood biochemistry was found to reduce the neutral fat (TG) concentration after ingestion in the capsule group (Table 9).

TABLE 8

Individual data representing results of blood test before and after ingestion of subjects in the capsule group and the can group

| Items | Before ingestion | After ingestion |
|---|---|---|
| Capsule group | | |
| WBC | 4978.3 ± 1428.0 | 4952.2 ± 1254.8 |
| RBC | 452.7 ± 31.7 | 446.3 ± 31.3 |
| Hb | 13.0 ± 1.6 | 12.9 ± 1.7 |
| Ht | 41.6 ± 4.4 | 41.1 ± 4.1 |
| MCV | 91.9 ± 6.6 | 92.1 ± 6.7 |
| MCH | 28.8 ± 2.9 | 28.9 ± 3.0 |
| MCHC | 31.2 ± 1.5 | 31.3 ± 1.4 |
| Number of thrombocyte | 28.2 ± 5.5 | 26.8 ± 5.0 |
| Can group | | |
| WBC | 5045.8 ± 1472.3 | 5004.2 ± 1121.5 |
| RBC | 454.1 ± 6.2 | 449.2 ± 34.0 |
| Hb | 13.7 ± 0.9 | 13.6 ± 1.1 |
| Ht | 42.9 ± 2.7 | 42.7 ± 3.4 |
| MCV | 94.6 ± 3.0 | 95.0 ± 2.8 |
| MCH | 30.2 ± 0.9 | 30.2 ± 0.9 |
| MCHC | 32.0 ± 1.1 | 31.8 ± 0.9 |
| Number of thrombocyte | 26.6 ± 5.1 | 25.9 ± 6.4 |

Each value in the table represents an average +/− standard deviation.

TABLE 9

Individual data representing results of blood biochemistry test before and after ingestion of subjects in capsule group and the can group

| Items | Before ingestion | After ingestion |
|---|---|---|
| Capsule group | | |
| Glucose (mg/dL) | 90.9 ± 11.1 | 88.4 ± 7.2 |
| NEFA (mg/dL) | 319.4 ± 201.7 | 445.4 ± 302.0 |
| TP (g/dL) | 7.1 ± 0.1 | 7.0 ± 0.3 |
| HDL-C (mg/dL) | 66.9 ± 12.2 | 65.8 ± 12.5 |
| LDL-C (mg/dL) | 90.6 ± 19.2 | 92.7 ± 18.2 |
| RLP-C (mg/dL) | 3.1 ± 1.2 | 2.8 ± 1.1* |
| Alb (g/dL) | 4.5 ± 0.3 | 4.5 ± 0.2 |
| TG (mg/dL) | 59.7 ± 22.7 | 52.6 ± 21.2* |
| TC (mg/dL) | 168.0 ± 17.2 | 171.2 ± 19.9 |
| UN (mg/dL) | 12.8 ± 3.5 | 12.9 ± 3.8 |
| Cre (mg/dL) | 0.7 ± 0.1 | 0.7 ± 0.1 |
| UA (mg/dL) | 4.2 ± 0.7 | 4.2 ± 0.7 |
| Na (mEQ/L) | 141.1 ± 1.3 | 140.8 ± 0.9 |
| Cl (mEQ/L) | 105.3 ± 1.4 | 106.0 ± 1.3 |
| K (mEQ/L) | 4.2 ± 0.3 | 4.1 ± 0.2 |
| AST (U/L) | 17.2 ± 2.7 | 16.8 ± 2.3 |
| ALT (U/L) | 11.8 ± 3.6 | 12.0 ± 3.0 |
| LDH (U/L) | 141.5 ± 25.9 | 137.6 ± 21.9 |
| ALP (U/L) | 173.0 ± 42.0 | 165.9 ± 33.7 |
| γ-GTP (U/L) | 14.7 ± 9.3 | 13.4 ± 4.9 |
| Can group | | |
| Glucose (mg/dL) | 93.8 ± 7.8 | 92.7 ± 6.8 |
| NEFA (mg/dL) | 376.0 ± 186.8 | 365.9 ± 135.8 |
| TP (g/dL) | 7.2 ± 0.4 | 7.2 ± 0.5 |
| HDL-C (mg/dL) | 72.3 ± 17.4 | 69.6 ± 14.5 |
| LDL-C (mg/dL) | 96.2 ± 21.9 | 96.8 ± 22.7 |
| RLP-C (mg/dL) | 3.3 ± 1.3 | 2.8 ± 1.1 |
| Alb (g/dL) | 4.5 ± 0.3 | 4.5 ± 0.3 |
| TG (mg/dL) | 56.3 ± 22.0 | 49.1 ± 15.4 |
| TC (mg/dL) | 178.5 ± 33.0 | 178.6 ± 29.8 |
| UN (mg/dL) | 12.0 ± 3.2 | 12.8 ± 2.6 |
| Cre (mg/dL) | 0.7 ± 0.1 | 0.7 ± 0.1 |
| UA (mg/dL) | 4.5 ± 0.7 | 4.6 ± 1.0 |
| Na (mEQ/L) | 140.4 ± 1.2 | 140.9 ± 1.5* |
| Cl (mEQ/L) | 104.0 ± 1.6 | 104.6 ± 1.7 |
| K (mEQ/L) | 4.3 ± 0.3 | 4.3 ± 0.2 |
| AST (U/L) | 23.5 ± 20.2 | 17.4 ± 3.6 |
| ALT (U/L) | 16.2 ± 10.1 | 13.1 ± 4.2* |
| LDH (U/L) | 175.5 ± 52.0 | 160.8 ± 35.5 |
| ALP (U/L) | 190.8 ± 74.6 | 176.4 ± 47.7 |
| γ-GTP (U/L) | 15.0 ± 6.8 | 15.5 ± 7.0 |

Each value in the table represents an average +/− standard deviation.

(Example 2) Intervention Study 2

(1) Test Method (a) Test Food Product: the capsule of saury oil contained 0.35 g of fish oils derived from saury containing about 29% of LC-MUFA to all fatty acids. The capsule of blended oil contained 0.35 g of mixed oil containing tuna oil and purified olive oil at the weight ratio of 1:1 (containing LC-MUFA to all fatty acids in the ratio of about 1.8%). The total of EPA+DPA+DHA in the fatty acid composition of the capsule of saury oil and the capsule of blended oil was 19.4% and 19.7%, respectively, which were approximately equivalent.

The fatty acid compositions in the capsule of saury oil and the capsule of blended oil are shown in Table 10. The fatty acid composition was calculated by the value measured by gas chromatography after esterifying the ingredient in the composition according to AOCS official method Ce1b-89.

TABLE 10

| Capsule of saury oil | | Capsule of blended oil | |
| --- | --- | --- | --- |
| Fatty acid | Fatty acid composition (%) | Fatty acid | Fatty acid composition (%) |
| C14:0 | 6.7 | C14:0 | 1.0 |
| C15:0 | 0.8 | C15:0 | 0.2 |
| C16:0 | 11.2 | C16:0 | 9.7 |
| C16:1n-7 | 2.7 | C16:1n-7 | 2.5 |
| C18:0 | 1.7 | C18:0 | 3.0 |
| C18:1n-9 | 5.2 | C18:1n - 9 | 47.3 |
| C18:1n-7 | 1.0 | C18:1n-7 | 2.1 |
| C18:2n-6 | 1.7 | C18:2n-6 | 4.6 |
| C18:3n-3 | 1.6 | C18:3n-3 | 0.7 |
| C18:4n-3 | 5.9 | C18:4n-3 | 0.5 |
| C20:0 | 0.2 | C20:0 | 0.3 |
| C20:1n-11 | 10.3 | C20:1n-11 | 0.2 |
| C20:1n-9 | 2.7 | C20:1n-9 | 1.0 |
| C20:1n-7 | 0.2 | C20:1n-7 | 0.1 |
| C20:4n-6 | 0.6 | C20:3n-6 | 0.1 |
| C20:4n-3 | 1.2 | C20:4n-6 | 1.2 |
| C20:5n-3 | 6.3 | C20:5n-3 | 4.3 |
| C22:0 | 0.1 | C22:0 | 0.1 |
| C22:1n-11 | 15.4 | C22:1n-11 | 0.4 |
| C22:1n-9 | 0.6 | C22:1n-9 | 0.1 |
| C22:1n-7 | 0.2 | C22:1n-7 | 0.0 |
| C22:5n-3 | 1.3 | C22:5n-3 | 1.0 |
| C22:6n-3 | 11.8 | C22:6n-3 | 14.4 |
| others | 11.6 | others | 5.3 |
| LCMUFA | 29.4 | LCMUFA | 1.9 |
| EPA + DPA + DHA | 19.4 | EPA + DPA + DHA | 19.7 |

(b) Subjects: 52 healthy adult individuals including students of the Tokushima University having age of 20 or more were divided two groups (a saury oil capsule ingestion group and a blended oil capsule ingestion group). As the saury oil capsule ingestion group, 26 individuals having age of 21 in average (average weight: 54.2 kg (before ingestion) and 54.8 kg (after ingestion)) were participated in. As the blended oil capsule ingestion group, 26 individuals having age of 21 in average (average weight: 52.8 kg (before ingestion) and 53.0 kg (after ingestion)) were participated in (Table 11).

(c) Test condition: the subjects ingested 12 capsules per day for 4 weeks. The 12 capsules of saury oil contained 4.2 g of saury oil. The subjects would ingest about 1.1 g of LC-MUFA and about 0.7 g of n-3 polyunsaturated fatty acids (EPA+DPA+DHA) per day. The 12 capsules of blended oil contained 2.1 g of tuna oil and 2.1 g of purified olive oil. The subjects would ingest about 0.07 g of LC-MUFA per day and about 0.7 g of n-3 polyunsaturated fatty acids (EPA+DPA+DHA) per day. Thus, although the amount of ingestion of LC-MUFA in each capsule group was different, the amount of ingestion of n-3 polyunsaturated fatty acid (EPA+DPA+DHA) would be about the same.

Vascular endothelial function measurements were taken before the start of the study and at 4 weeks after ingestion. Vascular endothelial function was evaluated by measuring FMD values using a Flow Mediated Dilation (FMD) test device UNEX EF (manufactured by UNEX corporation). The FMD Value (%) was calculated by maximum expanded width (mm)/resting vessel diameter (mm)×100.

Statistical software Graphpad Prism (from MDF Co., Ltd.) was used for statistical processing. Multiple groups of tests were performed using a one-way variance analysis method, and a Tukey's multiple comparisons test was used for the multiple comparison test. For intergroup comparison between two groups, unpaired t-test which is an independent comparison of two groups was used. For intragroup comparison, paired t-test which is a dependent comparison of two groups was used.

(d) Run time: From Oct. 17, 2017 to Dec. 7, 2017

(2) Test Results (2-1) FMD Test

Figures 1, 2, 3, 4:
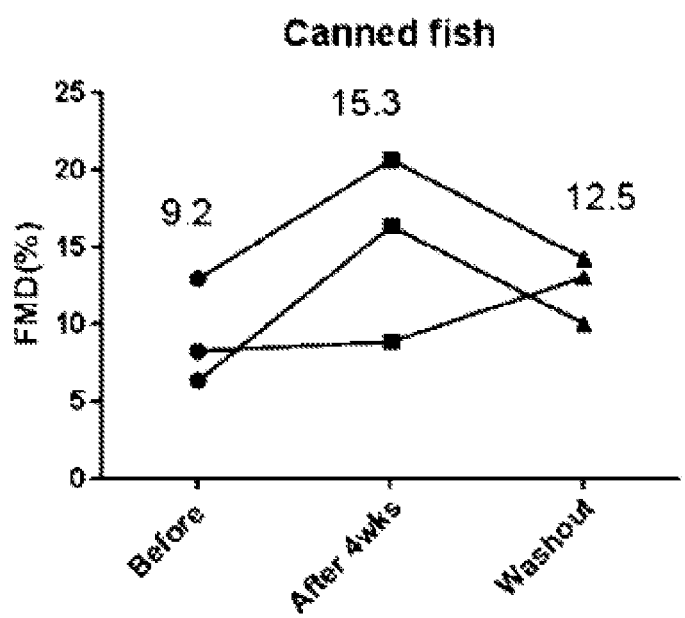
Figures 1, 2, 3, 4, 5:
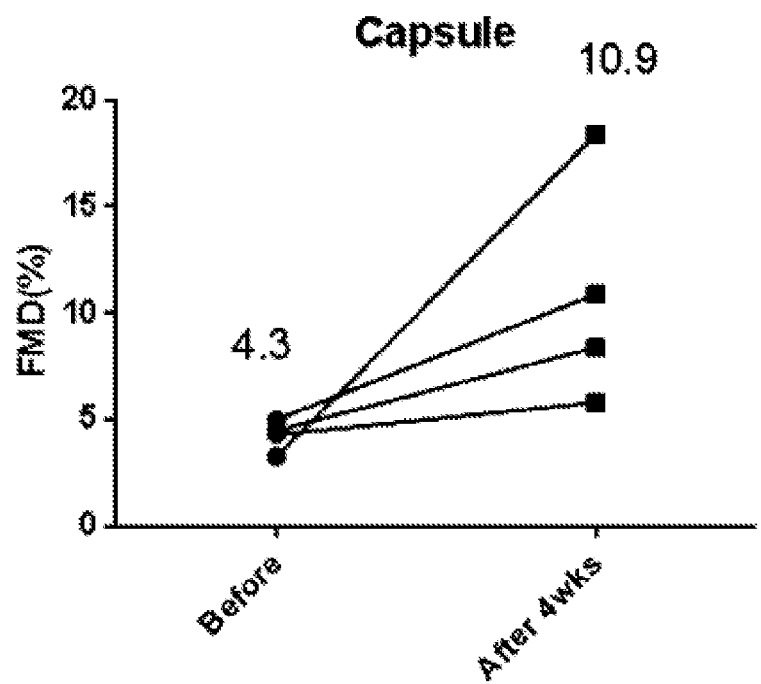
Figures 1, 2, 3, 4, 5, 6:
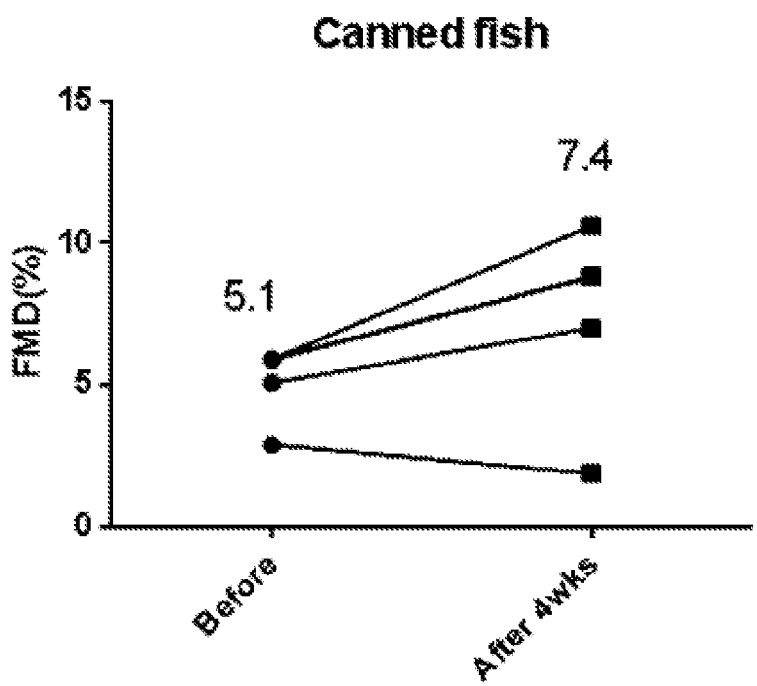
Figure 2:
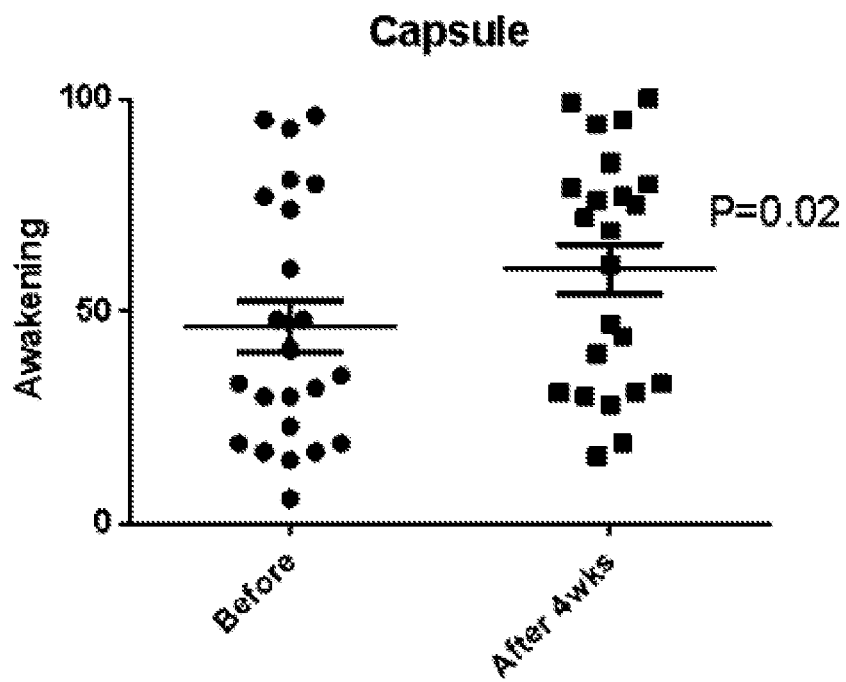
Figure 3:
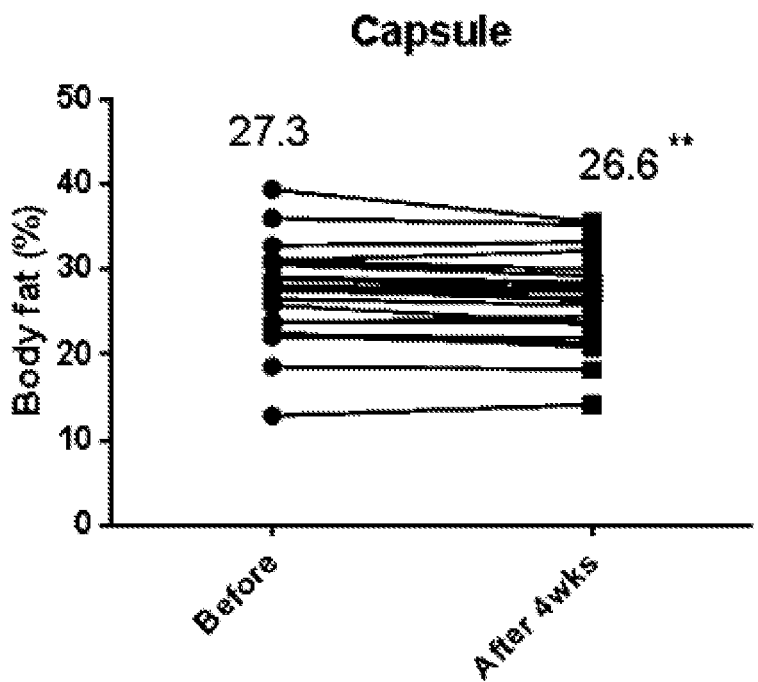
Figure 4:
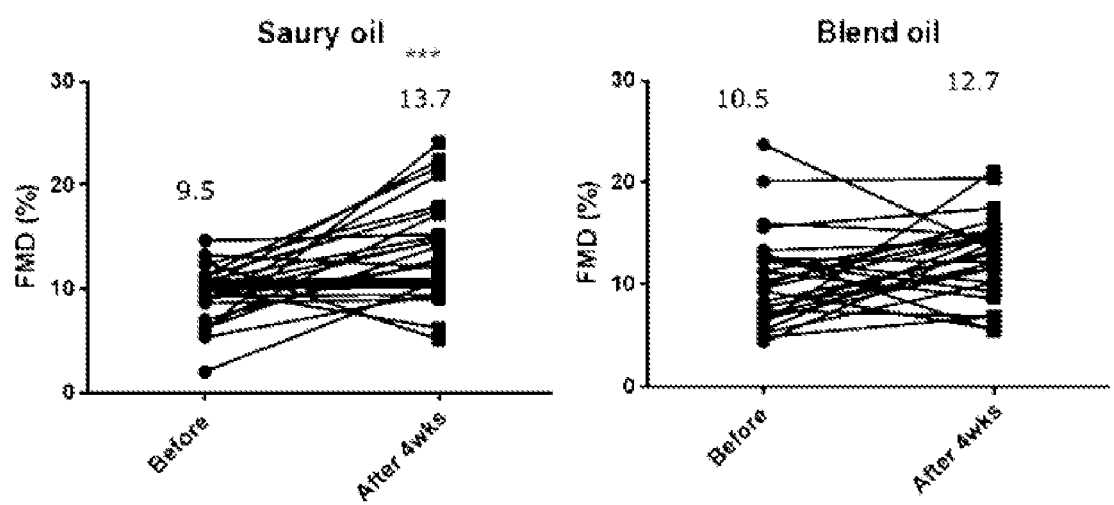

As shown in Table 11 and FIG. 4, in each group, the improvement of FMD values were observed compared to before ingestion at 4 weeks after the start of ingestion of the capsule. The improvement in FMD value of about 44% was observed in the saury oil capsule ingestion group. The improvement in FMD value of about 21% was observed in the blended oil capsule ingestion group. Since the amount of the n-3 polyunsaturated fatty acid was same in each capsule, the possibility of encouraging vascular endothelial function by the action of LC-MUFA was shown.

TABLE 11

Individual data representing changes in FMD values of subjects before and after ingestion in the saury oil capsule group and the blended oil capsule ingestion group

| Saury oil capsule group | | | Blended oil capsule group | | |
| --- | --- | --- | --- | --- | --- |
| ID | Before ingestion | After ingestion | ID | Before ingestion | After ingestion |
| 1 | 9.1 | 12.4 | 31 | 10.3 | 15 |
| 2 | 8.7 | 9.1 | 32 | 13.1 | 5.5 |
| 3 | 10.1 | 14.7 | 34 | 12.6 | 12.2 |
| 4 | 9.1 | 14.8 | 35 | 23.7 | 13.5 |
| 5 | 9.4 | 9.5 | 36 | 7.9 | 11.6 |
| 6 | 14.7 | 15.3 | 37 | 12.5 | 10.2 |
| 7 | 5.4 | 9.6 | 38 | 12.3 | 9.3 |
| 8 | 11.3 | 17.6 | 39 | 8.4 | 13 |
| 9 | 10.1 | 10.5 | 40 | 4.4 | 14.2 |
| 10 | 12.6 | 5.2 | 41 | 13.4 | 14.2 |
| 12 | 8.9 | 21 | 42 | 7.1 | 12.1 |
| 13 | 6.1 | 24.1 | 43 | 9.7 | 14.7 |
| 14 | 2.1 | 10.9 | 44 | 4.9 | 6.9 |
| 15 | 6.3 | 14.2 | 45 | 5.3 | 10.2 |
| 16 | 6.4 | 17.3 | 46 | 9.4 | 5.7 |
| 17 | 10.9 | 15.1 | 47 | 7.5 | 6.9 |
| 18 | 7.1 | 12.9 | 48 | 20.1 | 20.4 |
| 19 | 13.3 | 12.1 | 49 | 16 | 14.9 |
| 21 | 11.4 | 21.8 | 50 | 6.2 | 21.1 |
| 22 | 12.4 | 18 | 51 | 10 | 16.3 |
| 23 | 10 | 6.3 | 52 | 11.3 | 8.7 |
| 24 | 10.1 | 10.2 | 53 | 11.3 | 15.4 |
| 25 | 10.2 | 22.5 | 54 | 7.7 | 13.4 |
| 27 | 10.2 | 10.7 | 55 | 15.6 | 17.5 |
| 28 | 10.5 | 10.5 | 57 | 6.7 | 11.6 |
| 30 | 10.9 | 10.9 | 58 | 5.6 | 15 |
| Average value | 9.5 | 13.7 | Average value | 10.5 | 12.7 |

INDUSTRIAL APPLICABILITY

In accordance with the present invention, there is provided a food composition and a pharmaceutical composition that reduces the possibility of suffering from a disease due to vascular endothelial disorders. In accordance with the present invention, there is also provided a food composition and a pharmaceutical composition that improves wakefullness and quality of life.

The invention claimed is:

1. A method of improving vascular endothelial function, including:
administering a composition comprising an effective amount of an ingredient selected from a monounsaturated fatty acid having 20 carbon atoms or more, a salt thereof, and an ester thereof as an active ingredient to a human subject, wherein in the composition the ratio of the monounsaturated fatty acid having 20 carbon atoms or more to the total fatty acids in the composition is 10 wt % or greater, wherein the effective amount increases a flow-mediated dilatation value in the human subject, and wherein the active ingredient is orally administered to the human subject for four weeks or more in an amount from 2 mg/kg weight/day to 92 mg/kg weight/day, based on the monounsaturated fatty acid having 20 carbon atoms or more.

2. The method according to claim 1, wherein the active ingredient is an ingredient selected from a monounsaturated fatty acid having 20 carbon atoms, a salt thereof, and an ester thereof, an ingredient selected from a monounsaturated fatty acid having 22 carbon atoms, a salt thereof, and an ester thereof, or combinations thereof.

3. The method according to claim 1, wherein the active ingredient is a glyceride containing the monounsaturated fatty acid having 20 carbon atoms or more as a constituent fatty acid.

4. The method according to claim 3, wherein the glyceride is a triglyceride.

5. The method according to claim 1, wherein the composition further includes an n-3 polyunsaturated fatty acid and an n-6 polyunsaturated fatty acid, and wherein the area ratio of the n-3 polyunsaturated fatty acid to the n-6 polyunsaturated fatty acid is 4.0 or greater.

6. The method according to claim 1, wherein the active ingredient is derived from a fish oil.

7. The method according to claim 6, wherein the fish oil is a saury oil.

8. The method according to claim 1, including orally administering the active ingredient for four weeks or more in an amount of 20 mg/kg weight/day to 92 mg/kg weight/day, based on the monounsaturated fatty acid having 20 carbon atoms or more.

9. The method according to claim 1, wherein the effective amount reduces a possibility of suffering from a disease due to vascular endothelial disorders in the human subject.

10. The method according to claim 1, wherein the composition is a food composition.

11. The method according to claim 1, wherein the composition is a pharmaceutical composition.

* * * * *